United States Patent
Kang et al.

Patent Number: 5,187,288
Date of Patent: Feb. 16, 1993

[54] ETHENYL-SUBSTITUTED DIPYRROMETHENEBORON DIFLUORIDE DYES AND THEIR SYNTHESIS

[75] Inventors: Hee C. Kang; Richard P. Haugland, both of Eugene, Oreg.

[73] Assignee: Molecular Probes, Inc., Eugene, Oreg.

[21] Appl. No.: 704,287

[22] Filed: May 22, 1991

[51] Int. Cl.$^5$ .......................................... C07D 209/56
[52] U.S. Cl. ..................................... 548/110; 548/405
[58] Field of Search ............................... 548/110, 405

[56] References Cited

U.S. PATENT DOCUMENTS 4,774,339  9/1988  Haugland et al. ................. 548/110
4,916,711  4/1990  Boyer et al. ......................... 548/110

OTHER PUBLICATIONS

Treibs & Kreuzer *Difluorboryl-komplexe von di-und tripyrrylmethenen*, Liebigs Annalen Chem. 718, 203 (1968).

Worries, et al. *A novel water-soluble fluorescent probe:- Synthesis, luminescence and biological properties of the sodium salt of the 4-sulfonato-3,3',5,5'-tetramethyl-2,-2'-pyrromethen-1,1'-BF$_2$complex*, Recl. Trav. Chim. Pays-Bas 104, 288 (1985).

Pavlopoulos, et al., *Laser action from a tetramethylpyrromethene-BF$_2$ complex*, App. Optics 27, 4998 (1988).

Demas, J. N. & Crosby G. A. *The Measurement of Photoluminescence Quantum Yields* J. Phys. Chem. 75, 991 (1971).

K. C. Nicolaou, et al. *A Mild Method for the Synthesis of 2-Ketopyrroles from Carboxylic Acids* Tetrahedron Letters 22, 4647 (1981).

CA 112(18):160477v Reactive . . . biopolymers Haugland et al. 1988.

*Primary Examiner*—Mary C. Lee
*Assistant Examiner*—Joseph K. McKane
*Attorney, Agent, or Firm*—Allegra Helfenstein

[57] ABSTRACT

This invention relates to ethenyl-substituted derivatives of dipyrromethenepboron difluoride dyes that have an absorption maximum at wavelengths longer than about 525 nm, and are electrically neutral, highly photostable and, in most cases, highly fluorescent with relatively narrow absorption and emission spectra. The ethenyl-substituted dyes generally have the structure:

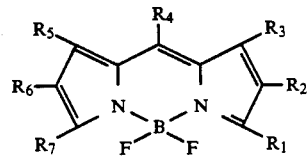

wherein at least one of the fluorophore substituents $R_1$-$R_7$, is an ethenyl group of the formula —$CX_m$=$CY_m$—$Z_m$, where m is any combination of locations 1, 2, 3, 4, 5, 6, and 7 corresponding to the location of parent fluorophore substituents $R_{1-7}$. The initial ethenyl substituents $X_m$, $Y_m$, and $Z_m$, which may be the same or different, are halogen, alkyl (containing 1-10 carbon atoms), cyano, ester, amide, ethenyl or polyethenyl, aryl or heteroaryl. The non-ethenyl substituents, which may be the same or different, are hydrogen, halogen, alkyl (containing 1-18 carbon atoms), aryl, arylalkyl, heteroaryl, acyl or sulfo.

20 Claims, 5 Drawing Sheets

ETHENYL-SUBSTITUTED DIPYRROMETHENEBORON DIFLUORIDE DYES AND THEIR SYNTHESIS

FIELD OF THE INVENTION

This invention relates to improvements in fluorescent dyes, particularly to dyes that are ethenyl-substituted derivatives of dipyrrometheneboron difluoride dyes (derivatives of ethenyl-4,4-difluoro-4-bora-3a,4a-diaza-s-indacene dyes) that have an absorption maximum at a wavelength longer than about 525 nm. These dyes have certain advantages over other dyes that absorb at these wavelengths of being electrically neutral, relatively photostable and being, in most cases, highly fluorescent with relatively narrow absorption and emission spectra.

BACKGROUND OF THE INVENTION

Fluorescent dyes have many uses and are known to be particularly suitable for biological applications in which the high detectability of fluorescence is required. Fluorescent dyes are used to impart both visible color and fluorescence to other materials.

Fluorescence useful for such applications is generally initiated by absorption of light from an external, relatively concentrated light source. The sensitivity of these applications is improved by having dyes that have high absorbance of the exciting light and high fluorescence quantum yield. The applications are furthermore improved by having dyes that resist photobleaching by the exciting light and that have spectral wavelengths in a range that avoids the background from contaminants that may be present in the samples. For many biological applications it is useful to have dyes whose fluorescence is not quenched by water, since most biological measurements are made in aqueous solution.

Certain lasers are particularly useful as a concentrated light source for the excitation of fluorescence. The argon laser has been the most common light source for excitation of fluorescence, with principal output at 488 nm and 514 nm. Now other lasers are increasingly used, such as helium-neon lasers that can be selected to have maximum output at either 543 nm, 594 nm, or 633 nm; the krypton laser which has significant output at 568 nm and 647 nm; and light emitting diodes which are available at this time with output commonly above 660 nm; resulting in increased demand for longer wavelength fluorescent dyes.

A number of dyes that have previously been found to be fluorescent do not have significant absorbance at desired longer excitation wavelengths. Many also have other characteristics which interfere with or limit their usefulness. For example, many known fluorescent dyes are significantly quenched in aqueous solution or are unstable during the illumination.

Dyes derived from dipyrrometheneboron difluoride have many desirable characteristics. Simple alkyl derivatives of the fluorophore 4,4-difluoro-4-bora-3a,4a-diaza-s-indacene have been described by Treibs & Kreuzer, Difluorboryl-komplexe von di- und tripyrrylmethenen, LIEBIGS ANNALEN CHEM. 718, 203 (1968) and by Worries, Kopek, Lodder, & Lugtenburg, A novel water-soluble fluorescent probe: Synthesis, luminescence and biological properties of the sodium salt of the 4-sulfonato-3,3',5,5'-tetramethyl-2,2'-pyrromethen-1,1'-BF$_2$ complex, RECL. TRAV. CHIM. PAYS-BAS 104, 288 (1985) as being highly fluorescent with spectral properties that are similar to fluorescein, with maximum absorbance at about 490 to 510 nm and maximum emission at about 500 to 530 nm.

U.S. Pat. No. 4,774,339 to Haugland et al. (1988) ('339 patent) describes 4,4-difluoro-4-bora-3a,4a-diaza-s-indacene (dipyrrometheneboron difluoride) dyes including hydrogen, halogen, alkyl, cycloalkyl, aryl, arylalkyl, acyl and sulfo-substituted derivatives that contain reactive groups suitable for conjugation to biomolecules, that have good photostability, and which have fluoresceinlike spectra.

As described in the '339 patent, and by Pavlopoulos, et al., Laser action from a tetramethylpyrromethene-BF$_2$ complex, APP. OPTICS 27, 4998 (1988), the emission of the alkyl derivatives of 4,4-difluoro-4-bora-3a,4a-diaza-s-indacene fluorescent dyes clearly overlaps that of fluorescein. The overlap allows the alkyl derivatives of dipyrrometheneboron difluoride to be used with the same optical equipment as used with fluorescein-based dyes without modification of the excitation sources or optical filters. As a result of having the same spectral characteristics, however, the fluorescence of the known class of alkyl-substituted 4,4-difluoro-4-bora-3a,4a-diaza-s-indacenes is not readily suitable for detection in combination with fluorescein or for use in applications where excitation by longer wavelength sources such as the helium-neon or krypton lasers or light emitting diodes is required.

U.S. Pat. No. 4,916,711 to Boyer, et al. (1990) ('711 patent) discloses a method of using derivatives of 4,4-difluoro-4-bora-3a,4a-diaza-s-indacene dyes, in particular symmetrical alkyl and sulfonated alkyl derivatives, as laser dyes. The '711 patent also discloses a multitude of possible alternatives for substituents of the basic tricyclic structure which can be used for the patented method. The '711 patent, however, is neither enabling nor prior art for the invention of ethenyl-substituted dipyrrometheneboron difluoride dyes. The '711 patent neither recognizes nor recites the effect or advantage of the alkenyl substitution in enhancing the long wavelength fluorescence properties of the dyes.

The novel dyes described in this invention contain one or more ethenyl groups directly coupled to the 4,4-difluoro-4-bora-3a,4a-diaza-s-indacene fluorophore through a single covalent bond ("ethenyl BDI dyes"). The ethenyl BDI dyes have significant absorbance and fluorescence at desired longer wavelengths, high fluorescence in aqueous solution and good photostability and are thus particularly useful as fluorescent dyes. Furthermore, the subject fluorescent dyes are desirable for use in combination with other fluorescent dyes such as fluorescein or alkyl-substituted 4,4-difluoro-4-bora-3a,4a-diaza-s-indacene dyes in that their fluorescence can be both selectively excited and detected because of their spectral shift to longer wavelengths, particularly an absorption maximum at greater than 525 nm and emission maximum at greater than 550 nm.

DESCRIPTION OF THE DRAWINGS

FIG. 1 is a general reaction scheme for synthesis of ethenyl BDI dyes. The general method consists of a formation of pyrromethene intermediates followed by cyclization with boron trifluoride in the presence of base to give ethenyl-substituted dipyrrometheneboron difluoride (ethenyl BDI) dyes.

SUMMARY OF THE INVENTION AND DESCRIPTION OF PREFERRED EMBODIMENTS

Figure 1A:
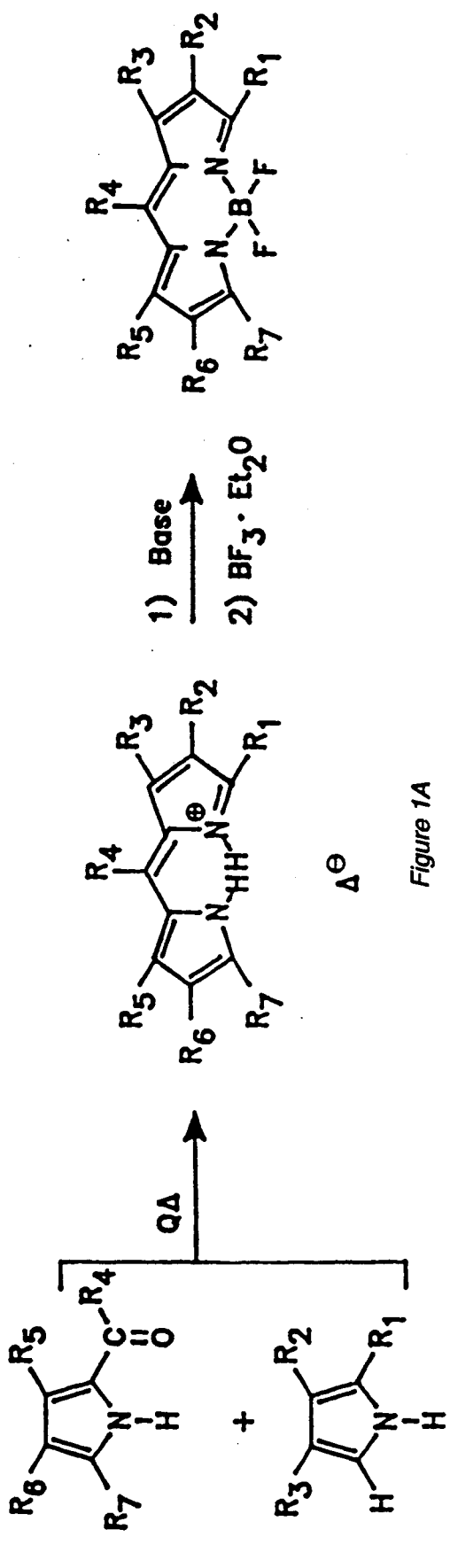
FIG. 1A shows a method of synthesis of asymmetric ethenyl BDI dyes. Condensation of an ethenyl pyrrole and a second pyrrole derivative having an aldehyde or ketone function at the 2-position, with an acid yields a pyrromethene intermediate. This pyrromethene intermediate is converted to an ethenyl BDI dye with boron trifluoride in the presence of base.
Figure 1B:
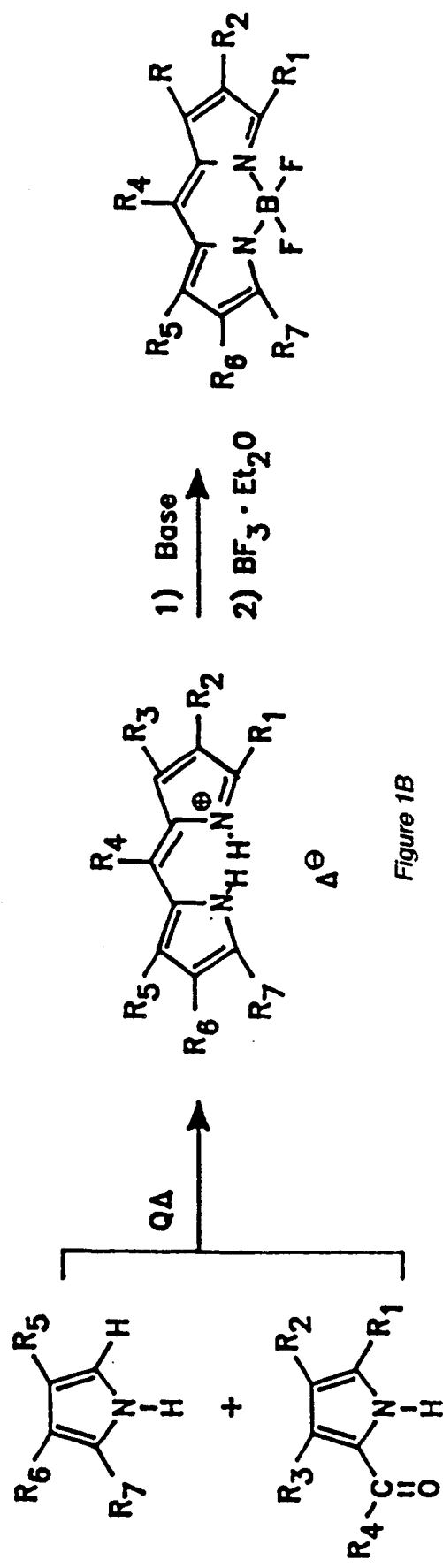
FIG. 1B also shows a synthetic scheme for asymmetric ethenyl BDI dyes. In this method, the ethenyl pyrrole contains the required aldehyde or ketone function which provides the methine bridge of the pyrromethene intermediate.
Figure 1C:
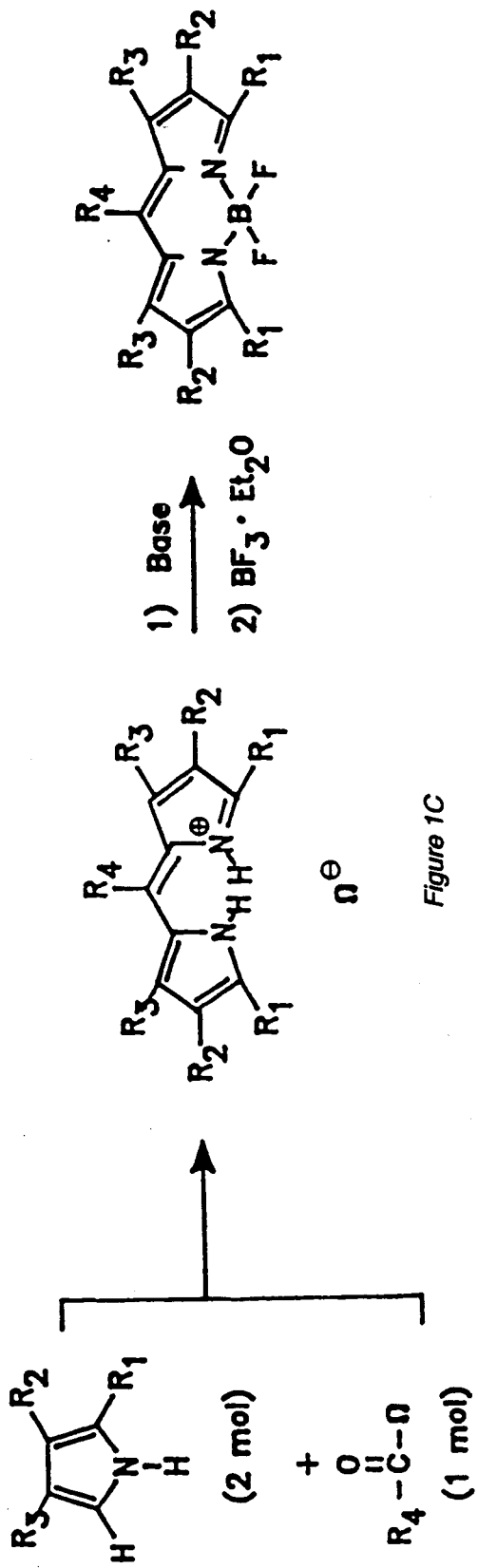
FIG. 1C gives a method for synthesis of symmetric ethenyl BDI dyes that contain two ethenyl substituents. Condensation of an ethenyl pyrrole having a hydrogen atom at the 2-position and a reactive carbonyl derivative yields a symmetric pyrromethene intermediate, which is further converted to a final product with boron trifluoride in the presence of a base.
Figure 1D:
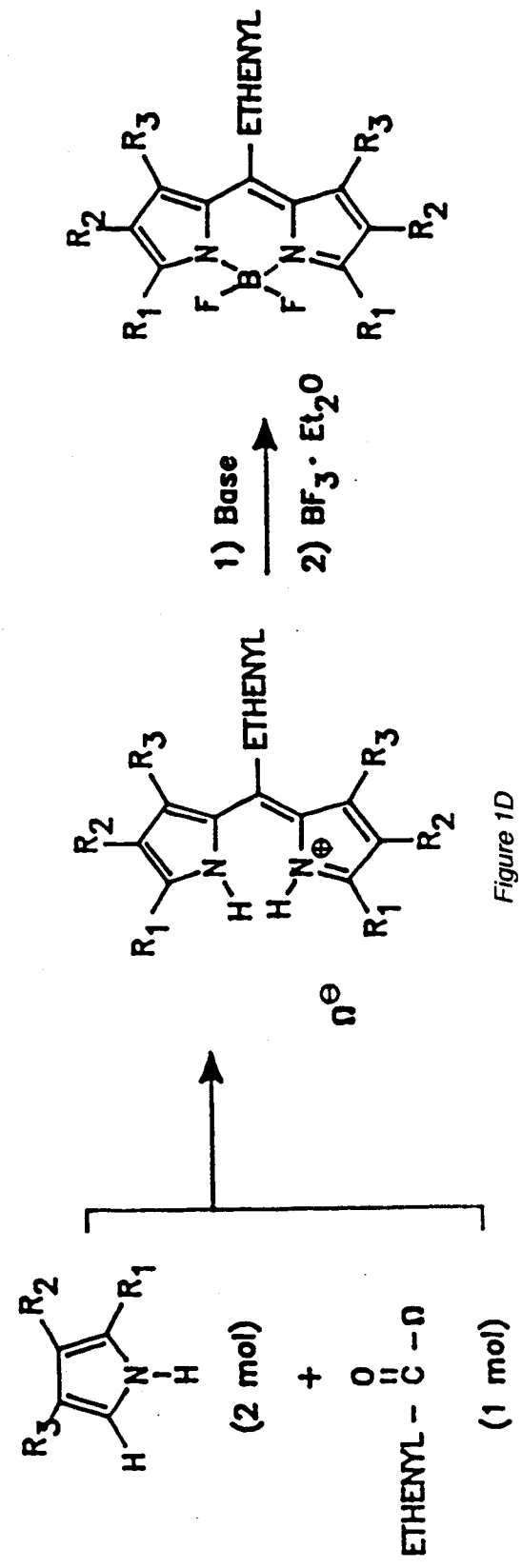
FIG. 1D shows a method for synthesis of symmetric dyes that contain an ethenyl substituent at the 8-position of the dyes. The ethenyl group is introduced into the meso-position of a pyrromethene intermediate by the use of an appropriate acrylic acid or aldehyde derivative.

This invention describes novel fluorescent dyes containing at least one ethenyl residue (—CX═CY—Z) conjugated to the 4,4-difluoro-4-bora-3a,4a-diaza-s-indacene ("BDI") fluorophore and methods for their synthesis. The ethenyl BDI dyes generally have the structure:

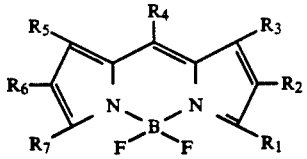

wherein any number of the substituents $R_1$–$R_7$ on the BDI fluorophore ("fluorophore substituents"), but at least one of such substituents, is an ethenyl group of the formula —CX$_m$═CY$_m$—Z$_m$. The initial ethenyl group is directly coupled to the BDI fluorophore through a single covalent bond. X$_m$, Y$_m$, and Z$_m$ are initial ethenyl substituents, where m can have any combination of the locations 1–7, corresponding to the parent fluorophore substituents $R_1$–$R_7$.

Typically, at least one of the fluorophore substituents $R_1$, $R_2$, $R_3$ or $R_4$ is an ethenyl group. Multiple ethenyl fluorophore substituents, in combinations of any of $R_1$–$R_7$, may be the same or different. In one embodiment of the invention, at least two of the fluorophore substituents $R_1$–$R_7$, which may be the same or different, are ethenyl residues.

The remainder of the fluorophore substituents $R_1$–$R_7$ that are not ethenyl groups are termed non-ethenyl fluorophore substituents. The non-ethenyl fluorophore substituents, which may be the same or different, are hydrogen, halogen, alkyl (containing 1-18 carbons), aryl, arylalkyl, the alkyl portions of which contain 1-18 carbon atoms, heteroaryl, acyl, or sulfo.

The initial ethenyl substituents X$_m$, Y$_m$, and Z$_m$ are hydrogen, halogen, alkyl (containing 1-10 carbon atoms), cyano, carboxylate ester, carboxamide, aryl or heteroaryl, or ethenyl to form a conjugated dienyl substituent. Any initial ethenyl substituent may be the same as any other ethenyl substituent, or they may all be different from each other. Preferably, one or two of X$_m$, Y$_m$, and Z$_m$ are hydrogen.

Any initial ethenyl substituent (X$_m$, Y$_m$, or Z$_m$) that is also ethenyl ("secondary ethenyl group") creates a conjugated dienyl substituent. The secondary ethenyl group has secondary ethenyl substituents X'$_{mp}$, Y'$_{mp}$, and Z'$_{mp}$ (in the formula —CX'$_{mp}$═CY'$_{mp}$—Z'$_{mp}$), where p designates the X, Y, or Z position of the secondary ethenyl group relative to the initial ethenyl substituent. Each secondary ethenyl substituent, which may be the same as or different from any other ethenyl substituent, is hydrogen, halogen, alkyl (containing 1-10 carbon atoms), cyano, carboxylate ester, carboxamide, aryl or heteroaryl, or ethenyl to form a conjugated trienyl substituent. Preferably one or two of X$_m$, Y$_m$ and Z$_m$ and one or two of X'$_{mp}$, and Y'$_{mp}$ and Z'$_{mp}$ are hydrogen.

Any secondary ethenyl substituent that is also ethenyl ("tertiary ethenyl group") creates a conjugated trienyl substituent. The tertiary ethenyl group has tertiary ethenyl substituents X"$_{mpt}$, Y"$_{mpt}$, and Z"$_{mpt}$ (in the formula —CX"$_{mpt}$—Z"$_{mpt}$), where the additional subscript t indicates which secondary position (X', Y', or Z') is substituted. The tertiary substituents, which may be the same or different, are hydrogen, halogen, alkyl (containing 1-10 carbon atoms), cyano, carboxylate ester, carboxamide, aryl or heteroaryl. Preferably one or two of X$_m$, Y$_m$ and Z$_m$, one or two of X'$_{mp}$, Y'$_{mp}$, and Z'$_{mp}$, and one or two of X"$_{mpt}$, Y"$_{mpt}$, and Z"$_{mpt}$, are hydrogen.

Aryl substituents preferred as fluorophore substituents (R) and as initial, secondary and tertiary substituents (X,Y,Z,X',Y',Z',X",Y",Z") are phenyl, 1-naphthyl, 2-naphthyl, 1-pyrenyl, 9-anthryl, and their alkoxy and dialkylamino substituted derivatives wherein the alkyl portions of such derivatives have less than 5 carbon atoms.

The term heteroaryl, as used throughout this document, means aromatic heterocyclic. When a heteroaryl group is present as a fluorophore substituent (R) or as initial, secondary or tertiary substituents (X,Y,Z,X-',Y',Z',X",Y",Z"), it is an aromatic heterocyclic substituent that contains at least one hetero atom (a non-carbon atom forming the ring structure) that is N, O, or S. A ring can be a 5- or 6-member ring. The heteroaryl group can be a single ring structure or a fused two- or three-ring structure. The heteroaryl group can contain one or more hetero atoms. Examples of heteroaryl substituents are pyrrole, thiophene, or furan (single ring, single hetero atom), or oxazole, isoxazole, oxadiazole, or imidazole (single ring, multiple hetero atoms). Alternatively, the heteroaryl group is a multi-ring structure containing one or more hetero atoms, for example, the heteroaryl substituent is benzoxazole, benzothiazole, or benzimidazole, (multi-ring, multiple hetero atoms), or benzofuran or indole (multi-ring, single hetero atom).

Any fluorophore substituent (R) and initial, secondary, and tertiary substituent (X,Y,Z, X',Y',Z',X",Y",Z") that is aryl or heteroaryl may be further substituted one or more times by alkyl (containing 1-5 carbons); or alkoxy or dialkylamino groups, the alkyl portions of which have less than 5 carbon atoms; or combinations thereof.

Any fluorophore substituent (R) and initial, secondary, and tertiary ethenyl substituent (X,Y,Z,X',Y',Z',X",Y",Z") that is alkyl may be further substituted by a substituent that is an ester or amide.

One preferred embodiment has the general formula BDI—$CX_m$=$CY_m$—$Z_m$(i.e. BDI with a single ethenyl residue), where BDI has the structure according to FORMULA I above and the single ethenyl residue is substituted as $R_1$, $R_2$,$R_3$, or $R_4$. The corresponding initial ethenyl substituents $X_m$ and $Y_m$ are hydrogen (m=1,2,3 or 4). The corresponding $Z_m$ (m=1,2,3 or 4) is alkyl (containing 1-5 carbons); cyano; carboxylate ester; carboxamide; aryl; heteroaryl; or aryl or heteroaryl further substituted one or more times by alkyl (containing 1-5 carbons), or alkoxy or dialkylamino groups the alkyl portions of which have less than 5 carbon atoms, or combinations of such further substituents. The remaining six non-ethenyl fluorophore substituents at $R_{1-7}$, which may be the same or different, are hydrogen; alkyl (containing 1-5 carbons); aryl or heteroaryl, which may be further substituted, one or more times, by alkyl (containing 1-5 carbons), or alkoxy or dialkylamino groups the alkyl portions of which have less than 5 carbon atoms, or combinations thereof.

In another preferred embodiment, there are two ethenyl groups symmetrically substituted on the BDI fluorophore at $R_1$ and $R_7$,$R_2$ and $R_6$, or $R_3$ and $R_5$ to give the general formula $Z_m$—$CY_m$=$CX_m$—BDI—$CX_m$=$CY_m$—$Z_m$. Again, BDI has the structure according to FORMULA I above. The corresponding $X_m$ and $Y_m$ substituents are hydrogen (m=1 and 7, 2 and 6, or 3 and 5). The corresponding $Z_m$ substituents (m=1 and 7, 2 and 6, or 3 and 5), which may be the same or different, are alkyl (containing 1-5 carbons); cyano; carboxylate ester; carboxamide; aryl; heteroaryl; or aryl or heteroaryl further substituted one or more times by alkyl (containing 1-5 carbons), or alkoxy or dialkylamino groups the alkyl portions of which have less than 5 carbon atoms, or combinations thereof. The remaining five non-ethenyl fluorophore substituents at $R_{1-7}$, which may be the same or different, are hydrogen; alkyl (containing 1-5 carbons); or aryl or heteroaryl, which may be further substituted, one or more times, by alkyl (containing 1-5 carbons), or alkoxy or dialkylamino groups the alkyl portions of which have less than 5 carbon atoms, or combinations thereof.

In yet another preferred embodiment, there are again two ethenyl groups symmetrically substituted at $R_1$ and $R_7$, $R_2$ and $R_6$, or $R_3$ and $R_5$. However, the corresponding initial ethenyl substituents $Z_m$ (m=1 and 7, 2 and 6, or 3 and 5), which may be the same or different, are ethenyl, thereby forming two conjugated dienyl substituents on the BDI fluorophore according to the formula $CZ'_{mZ}$—$CY'_{mZ}$=$CX'_{mZ}$—$CY_m$=$CX_m$—BDI—$CX_m$=$CY_m$—$CX'_{mZ}$=$CY'_{mZ}$—$Z'_{mZ}$. As previously, BDI has the structure according to FORMULA I above. The secondary ethenyl substituents $Z'_{mZ}$ (m=1 and 7, 2 and 6, or 3 and 5), which may be the same or different, are alkyl (containing 1-5 carbons); cyano; carboxylate ester; carboxamide; aryl; heteroaryl; or aryl or heteroaryl further substituted, one or more times, by alkyl (containing 1-5 carbons), or alkoxy or dialkylamino groups the alkyl portions of which have less than 5 carbon atoms, or combinations thereof. The corresponding initial and secondary ethenyl substituents $X_m$, $X'_{mZ}$, $Y_m$, and $Y'_{mZ}$ (m=1 and 7, 2 and 6, or 3 and 5) are hydrogen. The remaining five non-ethenyl fluorophore substituents at $R_{1-7}$, which may be the same or different, are hydrogen; alkyl (containing 1-5 carbons); or aryl or heteroaryl, which may be further substituted, one or more times, by alkyl (containing 1-5 carbons), or alkoxy or dialkylamino groups the alkyl portions of which have less than 5 carbon atoms, or combinations thereof.

In a further preferred embodiment, there is one ethenyl residue substituted at $R_1$, $R_2$, $R_3$, or $R_4$. The corresponding initial ethenyl substituent $Z_m$ (m=1,2,3 or 4) is ethenyl, thereby forming a single conjugated dienyl substituent according to the formula BDI—$CX_m$=$CY_m$—$CX'_{mZ}$=$CY'_{mZ}$—$Z'_{mZ}$, BDI having the structure of FORMULA I above. The corresponding initial and secondary ethenyl substituents $X_m$, $X'_{mZ}$, $Y_m$, and $Y'_{mZ}$ (m=1,2,3, or 4) are hydrogen. The corresponding secondary ethenyl substituent $Z'_{mZ}$ (m=1,2,3 or 4) is alkyl (containing 1-5 carbons); cyano; carboxy; aryl; heteroaryl; or aryl or heteroaryl further substituted, one or more times, by alkyl (containing 1-5 carbons), or alkoxy or dialkylamino groups the alkyl portions of which have less than 5 carbon atoms, or combinations thereof. The remaining six non-ethenyl fluorophore substituents at $R_{1-7}$, which may be the same or different, are hydrogen; alkyl (containing 1-5 carbons); or aryl or heteroaryl, which may be further substituted by alkyl (containing 1-5 carbons), or alkoxy or dialkylamino groups the alkyl portions of which have less than 5 carbon atoms, or combinations thereof.

Table 1 contains a sample of representative ethenyl BDI dyes.

Table 3 describes the physical properties of the representative dyes from Table 1.

Table 4 lists the NMR spectral data for the representative dyes from Table 1.

TABLE 1

EXAMPLES* OF NEW ETHENYL-SUBSTITUTED DIPYRROMETHENEBORON DIFLUORIDE DYES

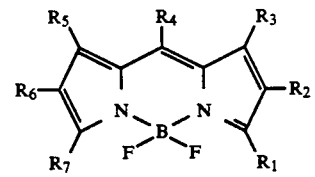

| COMPOUND | $R_1$ | $R_2$ | $R_3$ | $R_4$ | $R_5$ | $R_6$ | $R_7$ |
|---|---|---|---|---|---|---|---|
| 1 | PR | H | H | H | $CH_3$ | H | $CH_3$ |
| 2 | CNET | H | H | H | $CH_3$ | H | $CH_3$ |
| 3 | ST | H | H | H | $CH_3$ | H | $CH_3$ |
| 4 | 4-MST | H | H | H | $CH_3$ | H | $CH_3$ |
| 5 | 3-MST | H | H | H | $CH_3$ | H | $CH_3$ |
| 6 | TMST | H | H | H | $CH_3$ | H | $CH_3$ |
| 7 | IOXET | H | H | H | $CH_3$ | H | $CH_3$ |
| 8 | OXET | H | H | H | $CH_3$ | H | $CH_3$ |
| 9 | NAET | H | H | H | $CH_3$ | H | $CH_3$ |
| 10 | CMST | H | H | H | $CH_3$ | H | $CH_3$ |
| 11 | CMET | H | H | H | $CH_3$ | H | $CH_3$ |
| 12 | PHBD | H | H | H | $CH_3$ | H | $CH_3$ |
| 13 | ST | H | H | H | H | H | ST |
| 14 | ST | H | H | H | H | H | PYR |
| 15 | ST | H | H | H | H | H | IOXET |

TABLE 1-continued

| | | | | | | | |
|---|---|---|---|---|---|---|---|
| 16 | IOXET | H | H | H | Ph | H | Ph |
| 17 | ST | H | H | H | Ph | H | Ph |
| 18 | PHBD | H | H | H | H | H | PHBD |
| 19 | PHBD | H | H | H | H | H | ST |
| 20 | NAET | H | H | H | H | H | NAET |
| 39 | CMET | H | H | H | Ph | H | Ph |
| 40 | ST | H | H | CH$_3$ | H | H | ST |
| 41 | CH$_3$ | H | CH$_3$ | ST | CH$_3$ | H | CH$_3$ |
| 42 | PHET | H | H | H | CH$_3$ | H | CH$_3$ |
| 43 | THET | H | H | H | CH$_3$ | H | CH$_3$ |
| R | CH$_3$ | H | CH$_3$ | H | CH$_3$ | H | CH$_3$ |

*The examples are preferred, representative compounds only and are not intended to be exclusive.

Compound R is included as a standard example of an alkyl-substituted dipyrrometheneboron difluoride dye, for comparison.

The names and chemical structures of abbreviations used in this Table are shown immediately below.

PR: (E)-propen-1-yl,

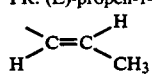

CNET: (Z)-2-cyanoethen-1-yl,

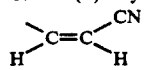

ST: (E)-2-phenylethen-1-yl,

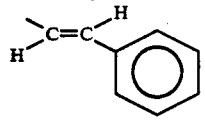

4-MST: (E)-2-(4-methoxyphenyl)ethen-1-yl,

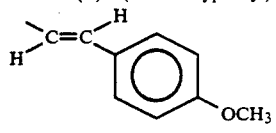

3-MST: (E)-2-(3-methoxyphenyl)ethen-1-yl,

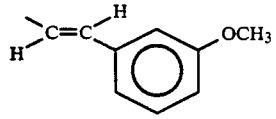

TMST: (E)-2-(3,4,5-trimethoxyphenyl)ethen-1-yl,

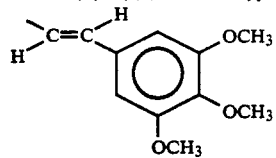

IOXET: (E)-2-(3,5-dimethyl-4-isoxazolyl)ethen-1-yl,

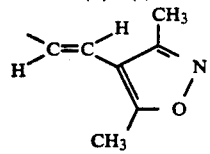

OXET: (E)-2-(5-carbomethoxy-4-methyl-2-oxazolyl)ethen-1-yl,

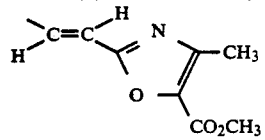

NAET: (E)-2-(1-naphthyl)ethen-1-yl,

CMST: (E)-2-(4-carbomethoxyphenyl)ethen-1-yl,

CMET: (E)-2-carbomethoxyethen-1-yl,

PHBD: 4-phenyl-1,3-butadien-1-yl,

—CH=CH—CH=CH—

Ph: phenyl,

PYR: 2-pyrrolyl,

PHET: 1-phenylethen-1-yl,

THET: 1-(2-thienyl)ethen-1-yl,

TABLE 3

PHYSICAL PROPERTIES OF REPRESENTATIVE NEW ETHENYL-SUBSTITUTED DIPYRROMETHENEBORON DIFLUORIDE DYES

| Compound | M.P. (°C.) | ABS$_{max}$ (mm)* | EM$_{max}$ (mm)* | R$_f$ | T.L.C. Solvent |
|---|---|---|---|---|---|
| 1 | 148–150 | 532.0 | 538 | 0.60 | A |
| 2 | 185–187 | 525.2 | 537 | 0.27 | A |
| 3 | 197–198 | 560.0 | 567 | 0.52 | A |
| 4 | 177–180 | 570.4 | 584 | 0.53 | A |
| 5 | 191–192 | 560.8 | 569 | 0.53 | A |
| 6 | 194–196 | 567.4 | 581 | 0.16 | A |
| 7 | 242–244 | 551.6 | 564 | 0.21 | A |
| 8 | 252–253 | 561.4 | 570 | 0.15 | A |
| 9 | 204–207 | 566.8 | 583 | 0.56 | A |
| 10 | 252–254 | 563.2 | 571 | 0.25 | A |
| 11 | 171–176 | 535.2 | 544 | 0.11 | A |
| 12 | 260–262 | 577.4 | 588 | 0.66 | A |
| 13 | 249–252 | 625.2 | 633 | 0.31 | B |

TABLE 3-continued

PHYSICAL PROPERTIES OF REPRESENTATIVE NEW
ETHENYL-SUBSTITUTED DIPYRROMETHENEBORON
DIFLUORIDE DYES

| Compound | M.P. (°C.) | $ABS_{max}$ (mm)* | $EM_{max}$ (mm)* | $R_f$ | T.L.C. Solvent |
|---|---|---|---|---|---|
| 14 | 163–165 | 638.4 | 651 | 0.32 | B |
| 15 | 235–238 | 619.6 | 628 | 0.25 | A |
| 16 | 251–253 | 588.8 | 609 | 0.27 | A |
| 17 | 205–206 | 594.4 | 612 | 0.47 | B |
| 18 | 276–278 | 665.2 | 676 | 0.36 | C |
| 19 | 224–226 | 642.8 | 655 | 0.27 | B |
| 20 | 256–258 | 640.6 | 665 | 0.69 | A |
| 39 | 155 (dec) | 575.2 | 591 | 0.27 | A |

*The absorption and emission maxima of the representative compounds were measured in methanol solution.
T.L.C. Solvent
A = Chloroform
B = 30% ethyl acetate in hexane
C = 50% ethyl acetate in hexane

TABLE 4

$^1$H NMR SPECTRAL DATA OF REPRESENTATIVE NEW ETHENYL-SUBSTITUTED DIPYRROMETHENEBORON DIFLUORIDE DYES

| COMPOUND | CHEMICAL SHIFT IN PPM IN CDCl$_3$ (300 MHz NMR) |
|---|---|
| 1 | 2.00(d, 3H, CH$_3$), 2.25(s, 3H, CH$_3$), 2.60(s, 3H, CH$_3$), 6.11(s, 1H, ArH), 6.61(m, 1H, CH=), 6.67(d, 1H, ArH), 6.92(d, 1H, ArH), 6.99(d, 1H, CH=), 7.05(s, 1H, ArCH=). |
| 2 | 2.29(s, 3H, CH$_3$), 2.61(s, 3H, CH$_3$), 5.46(d, 1H, CH=), 6.25(s, 1H, ArH), 6.91(d, 1H, ArH), 7.15(s, 1H, ArCH=), 7.48(d, 1H, ArH), 7.63(d, 1H, CH=). |
| 3 | 2(s, 3H, CH$_3$), 2.61(s, 3H, CH$_3$), 6.12(s, 1H, ArH), 6.86(d, 1H, ArH), 6.95(d, 1H, ArH), 7.05(s, 1H, ArCH=), 7.22-7.4(m, 3H, 3xArH), 7.27(d, 1H, CH=). |
| 4 | 2.25(s, 3H, CH$_3$), 2.60(s, 3H, CH$_3$), 3.84(s, 3H, CH$_3$), 6.10(S, 1H, ArH), 6.83(d, 1H, ArH), 6.90(d, 2H, 2xArH), 6.94(d, 1H, ArH), 7.02(s, 1H, ArCH=), 7.24(d, 1H, ArCH=), 7.24(d, 1H, CH=), 7.51(d, 1H, CH=), 7.55(d, 2H, 2xArH). |
| 5 | 2.26(s, 3H, CH$_3$), 2.61(s, 3H, CH$_3$), 3.86(s, 3H, CH$_3$), 6.12(s, 1H, ArH), 6.85(d, 1H, ArH), 6.87(d, 1H, ArH), 6.94(d, 1H, ArH), 7.05(s, 1H, ArCH=), 7.10(s, 1H, ArH), 7.21(d, 1H, ArH), 7.25-7.30(m, 1H, ArH), 7.29(d, 1H, CH=), 7.62(d, 1H, CH=). |
| 6 | 2.28(s, 3H, CH$_3$), 2.61(s, 3H, CH$_3$), 3.90(s, 3H, CH$_3$), 3.93(s, 6H, 2xCH$_3$), 6.15(d, 1H, ArH), 6.82(s, 2H, 2xArH), 6.87(d, 1H, ArH), 6.97(d, 1H, ArH), 7.07(s, 1H, ArCH=), 7.23(d, 1H, CH=), 7.55(d, 1H, CH=). |
| 7 | 2.26(s, 3H, CH$_3$), 2.47(s, 3H, CH$_3$), 2.55(s, 3H, CH$_3$), 2.59(s, 3H, CH$_3$), 6.13(s, 1H, ArH), 6.78(d, 1H, ArH), 6.92(d, 1H, CH=), 6.94(d, 1H, ArH), 7.06(s, 1H, ArCH=), 7.37(d, 1H, CH=). |
| 8 | 2,28(s, 3H, CH$_3$), 2.51(s, 3H, CH$_3$), 2.64(s, 3H, CH$_3$), 3.94(s, 3H, CH$_3$), 6.20(s, 1H, ArH), 6.83(d, 1H, ArH), 6.91(d, 1H, ArH), 7.00(d, 1H, CH=), 7.10(s, 1H, ArCH=), 8.02(d, 1H, CH=). |
| 9 | 2.28(s, 3H, CH$_3$), 2.61(s, 3H, CH$_3$), 6.14(s, 1H, ArH), 7.00(s, 2H, 2xArH), 7.09(s, 1H, ArH), 7.49-7.57(m, 3H, 3xArH), 7.73(d, 1H, CH=), 7.84(d, 1H, ArH), 7.88(d, 1H, ArH), 7.95(d, 1H, ArH), 8.12(d, 1H, ArH), 8.23(d, 1H, ArH). |
| 10 | 2.27(s, 3H, CH$_3$), 2.62(s, 3H, CH$_3$), 3.93(s, 3H, CH$_3$), 6.15(s, 1H, ArH), 6.86(d, 1H, ArH), 6.95(d, 1H, ArH), 7.07(s, 1H, ArCH=), 7.26(d, 1H, CH=), 7.63(d, 2H, 2xArH), 7.70(d, 1H, CH=), 8.02(d, 2H, 2xArH). |
| 11 | 2.27(s, 3H, CH$_3$), 2.62(s, 3H, CH$_3$), 3.81(s, 3H, CH$_3$), 6.20(s, 1H, ArH), 6.47(d, H, CH=), 6.79(d, 1H, ArH), 6.87(d, 1H, ArH), 7.11(s, 1H, ArCH=), 8.00(d, 1H, CH=). |
| 12 | 2.25(s, 3H, CH$_3$), 2.60(s, 3H, CH$_3$), 6.11(s, 1H, ArH), 6.81(d, 1H, ArH), 6.93(d, 1H, ArH), 7.03(s, 1H, ArCH=), 7.45(d, 2H, 2xArH), the remaining seven protons are split between 6.75 and 7.38. |
| 13 | 6.94(d, 2H, 2xArH), 7.02(d, 2H, 2xArH), 7.04(s, 1H, ArCH=), 7.31-7.48(m, 6H, 6xArH), 7.36(d, 2H, 2xCH=), 7.66(d, 4H, 4xArH), 7.73(d, 2H, 2xCH=). |
| 14 | 6.39-6.42(m, 1H, ArH), 6.97(s, 1H, ArCH=), 7.21-7.23(m, 1H, ArH), 7.30(d, 1H, CH=), 7.62(d, 2H, 2xArH), 7.65(d, 1H, CH=), 10.47(bs, 1H, NH), the remaining seven protons are split between 6.84 and 7.45. |
| 15 | 2.52(s, 3H, CH$_3$), 2.58(s, 3H, CH$_3$), 6.86(d, 1H, ArH), 6.94(d, 1H, ArH), 6.97(d, 1H, ArH), 7.01(d, 1H, ArH), 7.03(s, 1H, ArCH=), the remaining nine protons are split between 7.31 and 7.70. |
| 16 | 2.48(s, 3H, CH$_3$), 2.51(s, 3H, CH$_3$), 6.73(s, 1H, ArH), 6.87(d, 1H, ArH), 7.00(d, 1H, CH=), 7.03(s, 1H, ArCH=), 7.04(d, 1H, ArH), 7.34(d, 1H, CH=), 7.44-7.60(m, 8H, 8xArH), 7.99(d, 2H, 2xArH). |
| 17 | 6.72(s, 1H, ArH), 6.97(d, 1H, ArH), 7.07(d, 1H, ArH), 7.38(s, 1H, ArCH=), 7.68(d, 1H, CH=), 8.00(d, 2H, 2xArH), the remaining fourteen protons are split between 7.25 and 7.63. |
| 18 | 6.98(d, 2H, 2xCH=), 7.12(d, 2H, 2xCH=), 7.17(d, 2H, 2xArH), 7.26(d, 2H, 2xArH), 7.63(d, 4H, 4xArH), the remaining eleven protons are split between 7.29 and 7.54. |
| 20 | 7.38(d, 2H, 2xArH), 7.56(d, 2H, 2xArH), 7.64(s, 1H, ArCH=), 7.93(d, 2H, 2xArH), 8.00(d, 4H, 4xArH), 8.49(d, 2H, 2xArH), 8.52(d, 2H, 2xCH=), the remaining eight protons are split between 7.58 and 7.71. |
| 39 | 3.84(s, 3H, CH$_3$), 6.54(d, 1H, CH=), 6.84(s, 1H, ArH), 6.89(d, 1H, ArH), 7.30(d, 1H, ArH), 7.35(s, 1H, ArCH=), 7.62-7.48(m, 8H, 8xArH), 8.02-8.09(m, 2H, 2xArH), 8.09(d, 1H, CH=). |

The additional electronic conjugation that results from incorporation of ethenyl substituents into the 4,4-difluoro-4-bora-3a,4a-diaza-s-indacene dye results in new ethenyl BDI dyes that have spectral properties that are significantly shifted from those of the related alkyl-substituted fluorophores, thus permitting their use in multi-color fluorescence applications in combination with fluorescein or alkyl-substituted 4,4-difluoro-4-bora-3a,4a-diaza-s-indacenes. Furthermore, this wavelength shift is usually accompanied by an increase in photostability of the ethenyl BDI dyes and in most cases by an increase in the extinction coefficient of the ethenyl BDI dyes relative to the alkyl-substituted 4,4-difluoro-4-bora-3a,4a-diaza-s-indacenes. The novel dyes have an absorption maximum at greater than about 525 nm and, preferably, an emission maximum at greater than about 550 nm.

Figure 4:
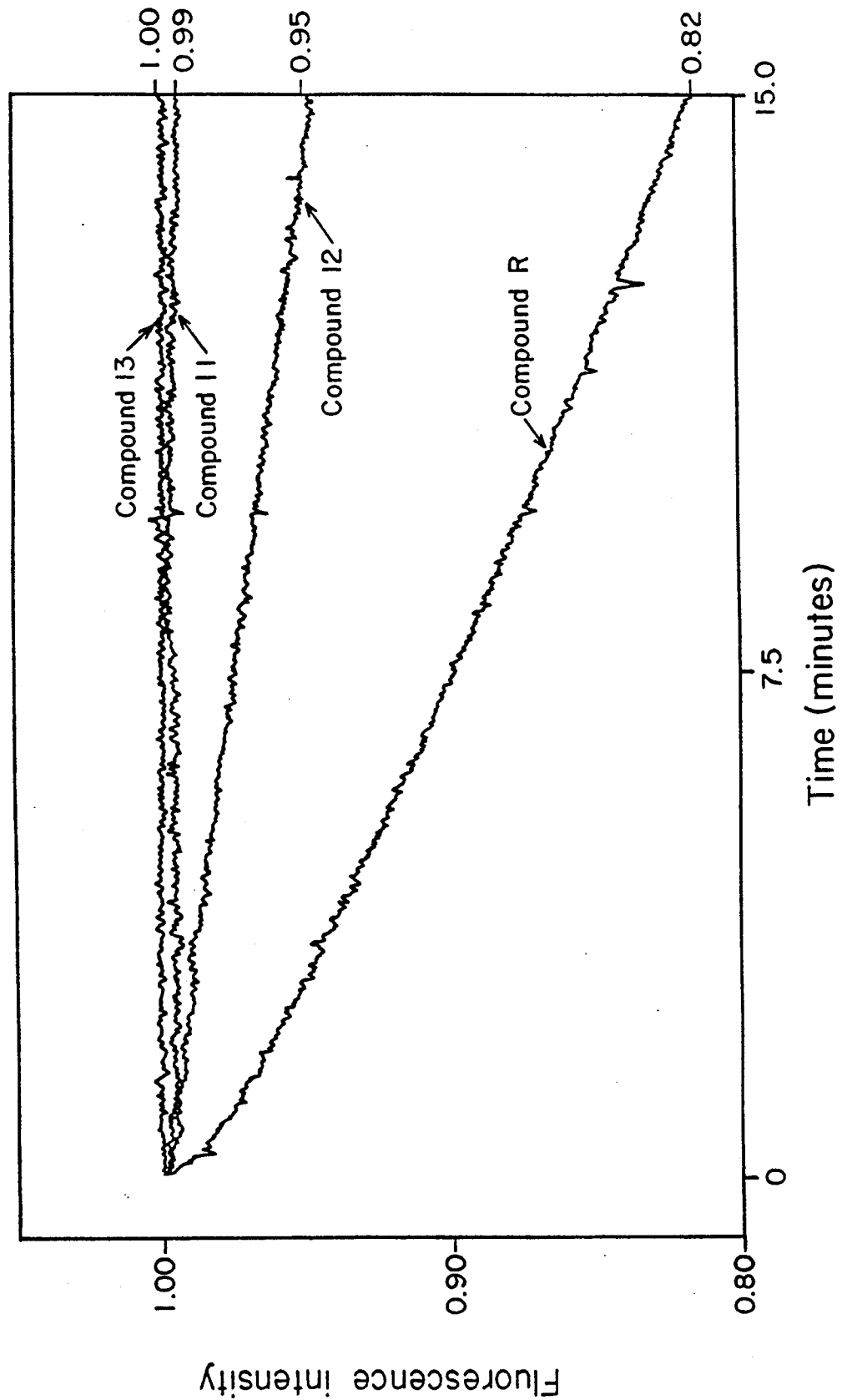
FIG. 4 is a graph showing the increased photostability of representative ethenyl BDI dyes in comparison with an alkyl-substituted dipyrrometheneboron difluoride dye, in CH$_3$CN solution.

These spectral properties distinguish the ethenyl BDI dyes from the related alkyl-substituted 4,4-difluoro-4-bora-3a,4a-diaza-s-indacene dyes. As indicated in Table 6 below, the absorption and emission spectra of the ethenyl BDI dyes are shifted to significantly longer wavelengths as compared to the alkyl-substituted dyes. The ethenyl BDI dyes also demonstrate improved photostability (Table 6, FIG. 4) relative to the alkyl-substituted dyes; with high extinction coefficients, generally greater than 90,000 cm$^{-1}$M$^{-1}$ (Table 6).

Figure 2:
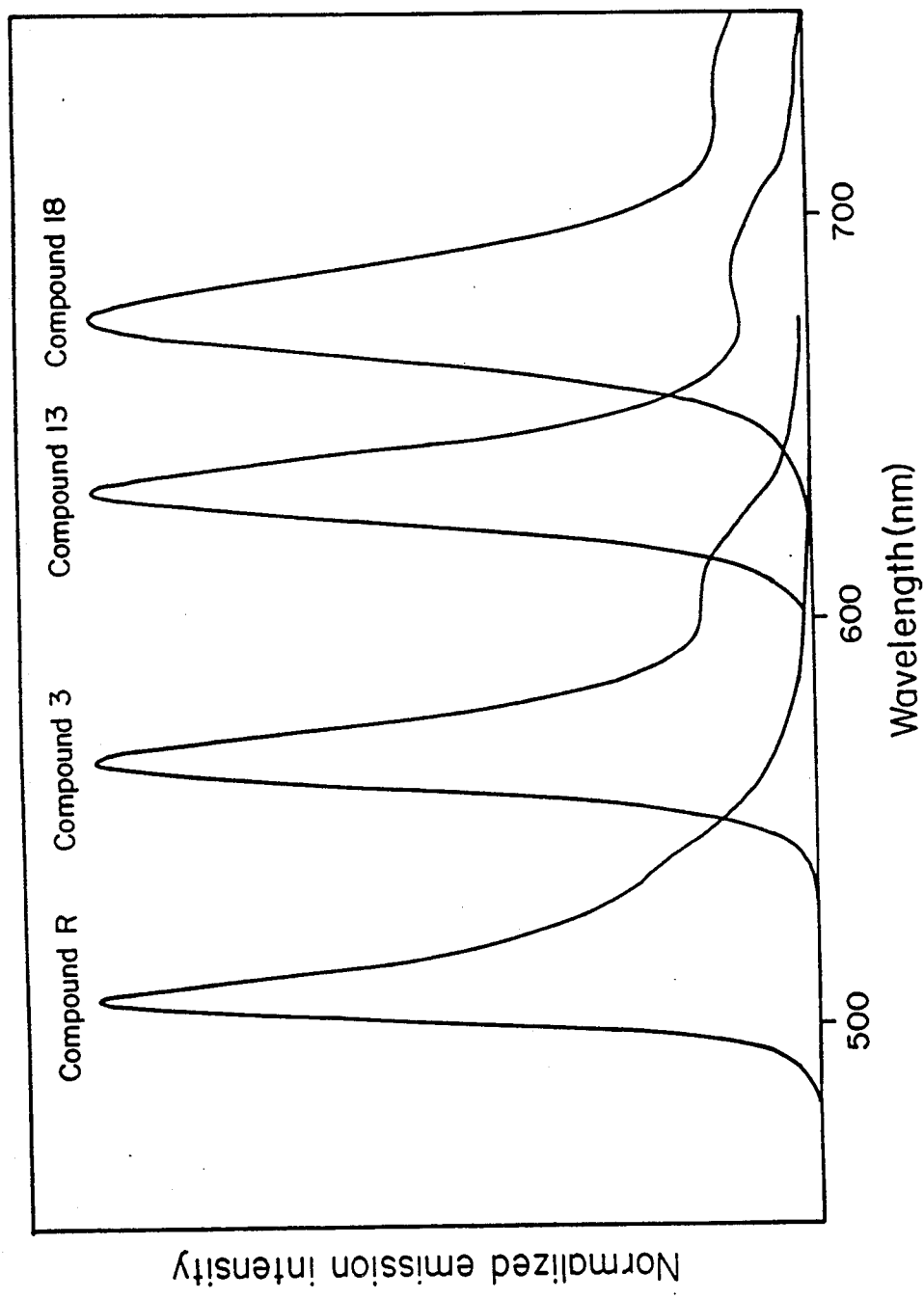
FIG. 2 is a graph of the relative spectral separations of selected examples of ethenyl BDI dyes in comparison with an alkyl-substituted dipyrrometheneboron difluoride dye, in methanol solution.
Figure 3:
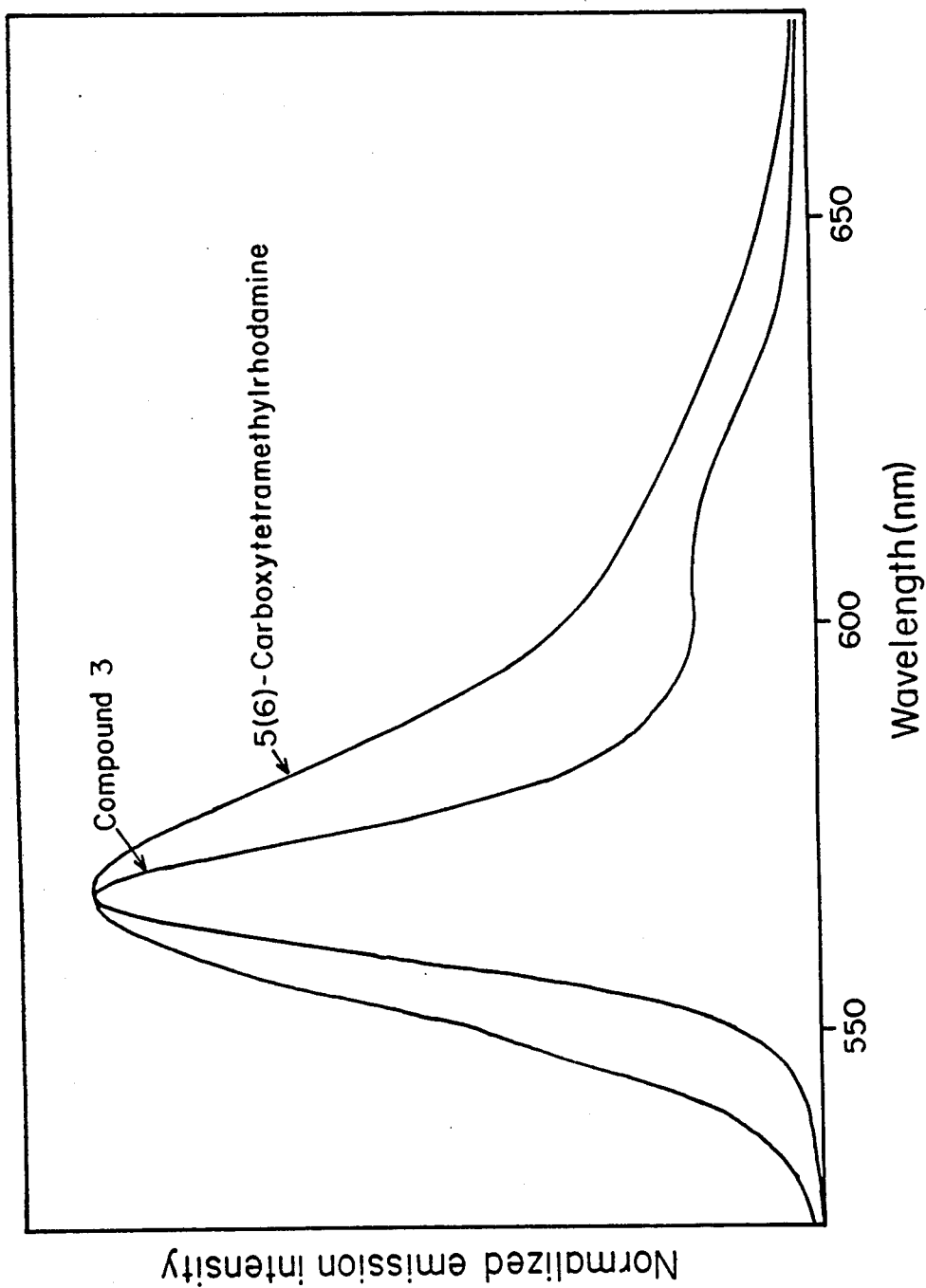
FIG. 3 is a graph showing the relatively narrow emission band width of a selected ethenyl BDI dye in comparison with another known dye emitting at the same wavelength (in methanol, excited at 540 nm).

Of further significance is the characteristic that the emission spectra of appropriate combinations of the dyes can be readily resolved (FIG. 2). This relatively high degree of spectral resolution is partly the result of the unusually narrow emission band width of the entire class of 4,4-difluoro-4-bora-3a,4a-diaza-s-indacene dyes relative to that of other important fluorophores in common use such as a tetramethylrhodamine derivative (FIG. 3). Furthermore, the fluorescence of the ethenyl BDI dyes is not usually quenched in aqueous solution. This general insensitivity of the dye to the environment of use increases the utility of these dyes in their applications.

Table 6 lists the spectral properties of representative examples of dyes from Table 1.

TABLE 6

SPECTRAL PROPERTIES OF SELECTED ETHENYL-SUBSTITUTED DIPYRROMETHENEBORON DIFLUORIDE DYES

| Compound | $\lambda_{max}^{Abs}$ (nm) | $\epsilon \times 10^{-3}$ (cm$^{-1}$M$^{-1}$) | $\lambda_{max}^{Em}$ (nm) | Quantum Yield ($\phi$) | Photostability |
|---|---|---|---|---|---|
| 3 | 568.4 | 128.2 | 575 | 1.00 | 0.95 |
| 11 | 544.0 | 93.9 | 553 | 1.00 | 0.99 |
| 12 | 588.4 | 153.7 | 596 | 1.00 | 0.95 |
| 13 | 636.5 | 156.1 | 644 | 0.88 | 1.00 |
| 18 | 679.2 | 178.1 | 688 | 0.46 | 1.00 |
| R* | 506.4 | 89.8 | 515 | 1.00 | 0.82 |

*Compound R is presented as an example of alkyl-substituted dipyrromethenboron difluoride dyes for comparison.

Absorption maxima ($\lambda_{max}^{Abs}$) and emission maxima ($\lambda_{max}^{Em}$) were measured in chloroform solution. Extinction coefficients ($\epsilon$) are shown in units of 10$^3$ × cm$^{-1}$M$^{-1}$ at their absorption maxima in chloroform solution.

Fluorescence quantum yields ($\phi$) in methanol were measured relative to rhodamine B ($\phi$ = 0.68) for Compounds, 3, 11, 12 and Nile Blue ($\phi$ = 0.25) for Compounds 13 and 18. Integrated fluorescence intensities were corrected for variation of solvent refractive index. The integrated fluorescence intensity was also corrected for variation of incident excitation light intensity with wavelength by recording spectra in a ratio mode relative to a rhodamine B/ethylene glycol quantum counter solution. Ref.: J. N. Demas & G. A. Crosby, J. PHYS. CHEM., 75, 991–1024 (1971).

Photostability data shows retention of emission intensity of dyes after continuous illumination at their excitation maxima for fifteen minutes in acetonitrile solution (see Example 32).

In general, there are two synthetic routes to ethenyl-substituted 4,4-difluoro-4-bora-3a, 4a-diaza-s-indacene dyes depending on whether the dyes are symmetric or asymmetric and each of these two routes has two variations (FIG. 1). Synthesis of ethenyl-substituted 4,4-difluoro-4-bora-3a,4a-diaza-s-indacene dyes requires the preparation of suitable pyrrole precursors substituted at the 2, 3 and/or 4 positions with at least one ethenyl substituent.

In the asymmetric synthesis of ethenyl-substituted 4,4-difluoro-4-bora-3a,4a-diaza-s-indacene dyes (FIG. 1A), this ethenyl pyrrole derivative is condensed in a reaction mediated by a suitable acid QΔ with a second pyrrole derivative that contains an aldehyde or ketone function in the 2-position used in approximately stoichiometric proportions to yield an intermediate pyrromethene salt. Suitable acids QΔ include, but are not limited to, hydrogen halides, metal salts typically used in Friedel-Crafts reactions such as zinc halides and non-metallic, electron deficient Lewis acids such as boron halides, halides of sulfur acids and phosphorous oxychloride in that such acids contain elements or groups of elements capable of forming an anionic counterion. Preferred is phosphorus oxychloride, since its use results in moderate to good yields of the ethenyl-substituted pyrromethene salts. In some cases it may be practical to use boron trifluoride as both the acid component and to complete formation of the 4,4-difluoro-4-bora-3a,4a-diaza-s-indacene dye in a "one-pot reaction". Cyclization of the heterocyclic ring with formation of the asymmetric ethenyl-substituted 4,4-difluoro-4-bora-3a,4a-diaza-s-indacene dye is completed by addition of boron trifluoride in combination with a suitable base (e.g. EXAMPLES 1, 2, 3, 4, 5, 6, 7, 8, 9, 10, 11, 12, 29, 30). Boron trifluoride is preferably used as one of its ether complexes because of the ease of handling these complexes rather than the gaseous reagent. Suitable bases include, but are not limited to trimethylamine, triethylamine, N,N-diisopropylethylamine, tetramethylethylenediamine, 1,8-bis(dimethylamino)naphthalene, diazabicyclooctane, and diazabicycloundecene, 4-dimethylaminopyridine and 4-pyrrolidinopyridine, and other similar bases.

In a variation of the asymmetric ethenyl-substituted 4,4-difluoro-4-bora-3a,4a-diaza-s-indacene dye synthesis (FIG. 1B), the ethenyl pyrrole can contain the required aldehyde or ketone substituent that is necessary to provide the methine bridge of the pyrromethene intermediate. This ethenyl pyrrole aldehyde or ketone is condensed in a reaction mediated by a suitable acid QΔ, with approximately stoichiometric proportions of a second pyrrole derivative to give an ethenyl-substituted pyrromethene salt (e.g. EXAMPLES 14, 15, 19, 24).

Alternatively, to produce symmetric ethenyl-substituted 4,4-difluoro-4-bora-3a,4a-diaza-s-indacene dyes that contain two ethenyl residues (FIG. 1C), ethenyl pyrrole derivatives that contain a hydrogen atom on the carbon in the 2 position are condensed with an aldehyde, an acid halide or a carbonyl derivative R—(C=O)—Ω that has been activated to electrophilic aromatic substitution reactions by incorporation of a residue Ω to increase the electron deficiency of the carbonyl group. The group —(C=O)—Ω defines an ester, amide, imide, anhydride or acid halide. In the case of Ω=H, the intermediate R—(C=O)—Ω is an aldehyde. In this case it is found that the ethenyl-substituted pyrromethene salt is still formed with the required oxidation coming from molecular oxygen or added oxidizing agents. The symmetric pyrromethene intermediate can be converted, by a source of boron trifluoride in combination with a base, to the symmetrically substituted 4,4-difluoro-4-bora-3a,4a-diaza-s-indacene dyes (e.g. EXAMPLE 27).

In a variation of the synthesis of a symmetric 4,4-difluoro-4-bora-3a,4a-diaza-s-indacene dye that contains a single ethenyl substituent (FIG. 1D), the ethenyl group is introduced into the 8 position of the 4,4-difluoro-4-bora-3a,4a-diaza-s-indacene dye by use of an appropriate aryl acrylic halide, aryl acrylic anhydride, or aryl acrolein derivative in the place of the acid halide or anhydride component (e.g. EXAMPLE 28).

Table 2 contains examples of pyrrole intermediates used to make dyes listed in Table 1.

Table 5 lists the melting point and spectral data of the intermediates shown in Table 2.

TABLE 2
EXAMPLES OF ETHENYL-SUBSTITUTED PYRROLE INTERMEDIATES

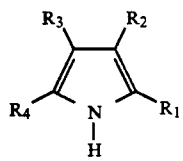

| COMPOUND* | $R_1$ | $R_2$ | $R_3$ | $R_4$ |
|---|---|---|---|---|
| 21 | PR | H | H | H |
| 22 | CNET | H | H | H |
| 23 | ST | H | H | H |

TABLE 2-continued
EXAMPLES OF ETHENYL-SUBSTITUTED PYRROLE INTERMEDIATES

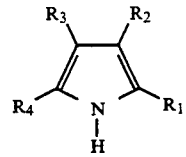

| COMPOUND* | $R_1$ | $R_2$ | $R_3$ | $R_4$ |
|---|---|---|---|---|
| 24 | 4-MST | H | H | H |
| 25 | 3-MST | H | H | H |
| 26 | TMST | H | H | H |
| 27 | IOXET | H | H | H |
| 28 | OXET | H | H | H |
| 29 | NAET | H | H | H |
| 30 | CMST | H | H | H |
| 31 | CMET | H | H | H |
| 32 | PHBD | H | H | H |
| 33 | ST | H | H | CHO |
| 34 | PHBD | H | H | CHO |
| 35 | NAET | H | H | CHO |
| 36 | CMET | H | H | CHO |
| 37 | PHET | H | H | H |
| 38 | THET | H | H | H |

*Substituents $R_1$—$R_4$ only refer to the pyrrole structure in this Table, and may not always coincide with the description in the text.
The names and chemical structures of abbreviations used in this Table are the same as those used in Table 1.

TABLE 5
M.P. AND $^1$H NMR SPECTRAL DATA OF ETHENYL-SUBSTITUTED PYRROLE INTERMEDIATES

| COMPOUND | M.P. (°C.) | CHEMICAL SHIFT IN PPM IN CDCl$_3$ (300 MHz NMR) |
|---|---|---|
| 21 | Oil | 1.80(d, 3H, CH$_3$), 5.76–5.90(m, 1H, CH=), 6.12–6.17(m, 1H, ArH), 6.19–6.25(m, 1H, ArH), 6.30(d, 1H, CH=), 6.70–6.77(m, 1H, ArH), 8.18(bs, 1H, NH). |
| 22 | Oil | 4.96(d, 1H, CH=), 6.29–6.31(m, 1H, ArH), 6.67–6.70(m, 1H, ArH), 6.95(m, 1H, ArH), 6.99–7.02(m, 1H, ArH), 9.72(bs, 1H, NH). |
| 23 | 139–141 | 6.25–6.29(m, 1H, ArH), 6.36–6.40(m, 1H, ArH), 6.67(d, 1H, CH=), 6.81–6.85(m, 1H, ArH), 6.99(d, 1H, CH=), 7.21–7.38(m, 3H, 3xArH), 7.44(d, 2H, 2xArH), 8.35(bs, 1H, NH). |
| 24 | 164–166 | 3.82(s, 3H, CH$_3$), 6.23–6.26(m, 1H, ArH), 6.29–6.32(m, 1H, ArH), 6.62(d, 1H, CH=), 6.79–6.82(m, 1H, ArH), 6.84(d, 1H, CH=), 6.88(d, 2H, 2xArH), 7.37(d, 2H, 2xArH), 8.30(bs, 1H, NH). |
| 25 | 75–76 | 3.84(s, 3H, CH$_3$), 6.24–6.28(m, 1H, ArH), 6.34–6.38(m, 1H, ArH), 6.63(d, 1H, CH=), 6.76–6.80(m, 1H, ArH), 6.95–7.05(m, 3H, 3xArH), 7.00(d, 1H, CH=), 7.22–7.28(m, 1H, ArH), 8.34(bs, 1H, NH). |
| 26 | 124–126 | 3.86(s, 3H, CH$_3$), 3.90(s, 6H, 2xCH$_3$), 6.24–6.27(m, 1H, ArH), 6.34–6.38(m, 1H, ArH), 6.61(d, 1H, CH=), 6.65(s, 2H, 2xArH), 6.80–6.84(m, 1H, ArH), 6.89(d, 1H, CH=), 8.43(bs, 1H, NH). |
| 27 | 78–81 | 2.36(s, 3H, CH$_3$), 2.45(s, 3H, CH$_3$), 6.23–6.26(m, 1H, ArH), 6.30–6.33(m, 1H, ArH), 6.33(d, 1H, CH=), 6.62(d, 1H, CH=), 6.80–6.83(m, 1H, ArH), 8.53(bs, 1H, NH). |
| 28 | 195–198 | 2.48(s, 3H, CH$_3$), 3.92(s, 3H, CH$_3$), 6.26–6.32(m, 1H, ArH), 6.45(d, 1H, CH=), 6.50–6.57(m, 1H, ArH), 6.90–6.96(m, 1H, ArH), 7.53(d, 1H, CH=), 8.66(bs, 1H, NH). |
| 29 | 120–121 | 6.29–6.32(m, 1H, ArH), 6.42–6.46(m, 1H, ArH), 6.86–6.89(m, 1H, ArH), 7.03(d, 1H, CH=), 7.44(d, 1H, CH=), 7.44–7.58(m, 3H, 3xArH), 7.68(d, 1H, ArH), 7.77(d, 1H, ArH), 7.86(d, 1H, ArH), 8.20(d, 1H, ArH), 8.46(bs, 1H, NH). |
| 30 | 120–121 | 3.90(s, 3H, CH$_3$), 6.26–6.29(m, 1H, ArH), 6.42–6.45(m, 1H, CH=), 6.68(d, 1H, CH=), 6.84–6.88(m, 1H, ArH), 7.08(d, 1H, CH=), 7.45(d, 2H, 2xArH), 7.99(d, 2H, 2xArH), 7.99(d, 2H, 2xArH), 8.55(bs, 1H, NH). |
| 31 | 124–126 | 3.79(s, 3H, CH$_3$), 6.05(d, 1H, CH=), 6.28–6.33(m, 1H, ArH), 6.55–6.60(m, 1H, ArH), 6.92–6.97(m, 1H, ArH), 7.57(d, 1H, CH=), 8.92(bs, 1H, NH). |
| 32 | 184–186 | 6.21–6.26(m, 1H, ArH), 6.30–6.35(m, 1H, ArH), 6.77–6.82(m, 1H, ArH), 7.44(d, 2H, 2xArH), 8.50(bs, 1H, NH), the remaining seven protons are split between 6.48 and 7.32. |
| 33 | 153–154 | 6.49–6.53 (m, 1H, ArH), 6.98–7.02(m, 1H, ArH), |

TABLE 5-continued

M.P. AND $^1$H NMR SPECTRAL DATA OF ETHENYL-SUBSTITUTED PYRROLE INTERMEDIATES

| COMPOUND | M.P. (°C.) | CHEMICAL SHIFT IN PPM IN CDCl$_3$ (300 MHz NMR) |
|---|---|---|
|  |  | 7.03(d, 1H, CH=), 7.18(d, 1H, CH=), 7.27–7.41(m, 3H, 3xArH), 7.50(d, 2H, 2xArH), 9.48(s, 1H, CHO), 10.56(bs, 1H, NH). |
| 34 | 218–220 | 6.41–6.43(m, 1H, ArH), 6.51(d, 1H, CH=), 6.72(d, 1H, CH=), 7.31–7.38(m, 2H, 2xArH), 7.45(d, 2H, 2xArH), 9.43(bs, 1H, NH), 9.46(s, 1H, CHO). The remaining four protons are split between 6.87 and 6.97. |
| 35 | 169–170 | 6.68(d, 1H, ArH), 7.06(d, 1H, ArH), 7.29(d, 1H, CH=), 7.50–7.60(m, 2H, 2xArH), 7.88(d, 2H, 2xArH), 7.92(d, 1H, ArH), 8.29(d, 1H, CH=), 8.41(d, 1H, ArH), 9.54(s, 1H, CHO). |

In general, ethenyl pyrrole precursors are prepared by Wittig reactions between an acyl pyrrole derivative and a Wittig reagent that contains the selected substituents X, Y, and Z, according to the following reaction scheme.

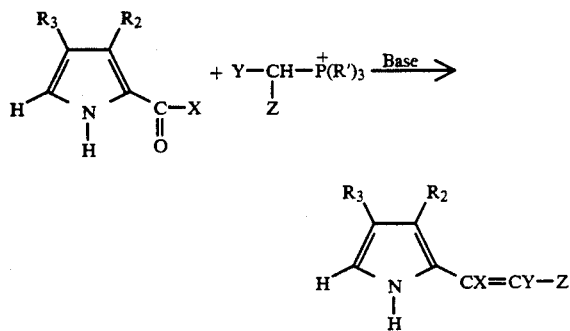

Typically (R')$_3$ is a triphenyl or a tri-n-butyl group. R$_2$ and R$_3$ correspond to the fluorophore substituents R$_2$ and R$_3$ of ethenyl BDI dyes. The substituents X, Y and Z, which may be the same or different, are hydrogen, halogen, alkyl (containing 1–10 carbon atoms), cyano, carboxylate ester, carboxamide, aryl or heteroaryl, and correspond to the ethenyl substituents X$_1$, Y$_1$, and Z$_1$ of the ethenyl BDI dyes when the ethenyl groups is substituted at R$_1$. The reaction scheme illustrates the incorporation of a single ethenyl group at the R$_1$ position, but can be modified appropriately for the prepartion of any precursor. Several methods for synthesis of ethenyl pyrrole precursors for ethenyl-substituted 4,4-difluoro-4-bora-3a,4a-diaza-s-indacene dyes are given in EXAMPLES 21, 22, 23, 24 and 25 described below. The Examples serve to illustrate the generality of the methods and properties of the ethenyl BDI dyes.

Among the substitutions exemplified on the ethenyl group are alkyl (EXAMPLE 1: methyl), carboxy (EXAMPLE 25) and its derivatives (EXAMPLES 11, 24: methyl ester), cyano (EXAMPLE 2), alkenyl (EXAMPLES 12, 18, 19), aryl (EXAMPLES 3, 13, 17: phenyl; EXAMPLES 4, 5, 6: methoxyphenyl derivatives; EXAMPLE 10: carbomethoxyphenyl; EXAMPLES 9, 20: naphthyl), heteroaryl (EXAMPLES 7, 15, 16: isoxazole; EXAMPLE 8: oxazole; EXAMPLE 14: pyrrole; EXAMPLE 30:thiophene).

Once prepared, the ethenyl-substituted 4,4-difluoro-4-bora-3a,4a-diaza-s-indacene dyes may be further modified by sulfonation, nitration, alkylation, acylation, halogenation and other reactions by methods known in the art, such as described by U.S. Pat. No. 4,916,711 to Boyer, et al. (1990) (the specification of which is incorporated by reference); Worries, et al., A novel water-soluble fluorescent probe: Synthesis, luminescence and biological properties of the sodium salt of the 4sulfonato-3,3',5,5'-tetramethyl-2,2'-pyrromethen-1,1'-BF$_2$ complex, RECL. TRAV. CHIM. PAYSBAS 104, 288 (1985) (incorporated by reference).

The resulting products are generally soluble in organic solvents. Aqueous solubility can be obtained by adding appropriate water solubilization groups that include sulfonates, carboxylates, ammonium and hydroxyl residues to the dyes. In most cases, the solid dyes are easily purified by techniques of chromatography and/or crystallization from a suitable solvent. The chemical structures of most representative examples of ethenyl BDI dyes have been confirmed by nuclear magnetic resonance spectroscopy (Table 4).

The following examples of the synthesis and characterization of the ethenyl BDI dyes is intended to illustrate the generality of the invention and not to define or limit the scope of the invention.

EXAMPLE 1

4,4-Difluoro-1,3-dimethyl-5-((E)-propen-1-yl)-4-bora-3a,4a-diaza-s-indacene

Compound 1

To a solution of 50 mg (0.41 mmol) of 3,5-dimethylpyrrole-2-carboxaldehyde and 44 mg (0.41 mmol) of 2-((E)-propen-1-yl)pyrrole, Compound 21, in 10 mL of dichloromethane is added 40 μL (0.43 mmol) of phosphorus oxychloride. The reaction mixture is stirred at room temperature for 3 hours and is added 250 μL (1.44 mmol) of N,N-diisopropylethylamine, followed by addition of 175 μL (1.42 mmol) of boron trifluoride etherate. After the whole mixture is stirred at room temperature for 2 hours, it is washed with two 10 mL portions of water. The organic layer is separated, dried over anhydrous sodium sulfate and concentrated under reduced pressure to give a brown oil. The crude product is purified by chromatography on silica gel with 1:1 hexane/chloroform as eluant to give 35 mg (33%) of Compound 1 as a red orange solid.

EXAMPLE 2

4,4-Difluoro-5,7-dimethyl-3-((Z)-2-cyanoethen-1-yl)-4-bora-3a,4a-diaza-s-indacene Compound 2

This is prepared in the same manner as described in Example 1 from 3,5-dimethylpyrrole-2-carboxaldehyde (100 mg, 0.81 mmol) and Compound 22, 2-((Z)-2-cyanoethen-1-yl)pyrrole (100 mg, 0.84 mmol). Compound 2 (31 mg, 14%) is obtained as a red orange solid.

EXAMPLE 3

4,4-Difluoro-1,3-dimethyl-5-((E)-2-phenylethen-1-yl)-4-bora-3a,4a-diaza-s-indacene Compound 3

To a solution of 36 mg (0.29 mmol) of 3,5-dimethylpyrrole-2-carboxaldehyde and 50 mg (0.30 mmol) of 2-((E)-2-phenylethen-1-yl)pyrrole, Compound 23, in 15 mL of dichloromethane is added 30 μL (0.32 mmol) of phosphorus oxychloride. The reaction mixture is stirred at room temperature for 12 hours and then is added 220 μL (1.26 mmol) of N,N-diisopropylethylamine followed by addition of 150 μL (1.22 mmol) of boron trifluoride etherate. After the whole reaction mixture is stirred at room temperature for 1 hour, it is washed with two 15 mL portions of water. The organic layer is separated, dried over anhydrous sodium sulfate and concentrated to give a reddish brown solid. The crude product is purified by chromatography on silica gel with 10% ethyl acetate in hexane as eluant to give 25 mg (27%) of the Compound 3 as a purple red solid.

EXAMPLE 4

4,4-Difluoro-1,3-dimethyl-5-((E)-2-(4-methoxyphenyl)ethen-1-yl)-4-bora-3a,4a-diaza-s-indacene Compound 4

This is prepared in the same manner as described in Example 3 from 3,5-dimethylpyrrole-2-carboxaldehyde (60 mg, 0.49 mmol) and 2-((E)-2-(4-methoxyphenyl)ethen-1-yl)pyrrole (Compound 24, 100 mg, 0.50 mmol). The Compound 4 (75 mg, 44%) is obtained as a dark purple solid.

EXAMPLE 5

4,4-Difluoro-1,3-dimethyl-5-((E)-2-(3-methoxyphenyl)ethen-1-yl)-4-bora-3a,4a-diaza-s-indacene Compound 5

This is prepared in the same manner as described in Example 3 from 3,5-dimethylpyrrole-2-carboxaldehyde (60 mg, 0.49 mmol) and 2-((E)-2-(3-methoxyphenyl)ethen-1-yl)pyrrole (Compound 25, 100 mg, 0.50 mmol). Compound 5 (64 mg, 37%) is obtained as a dark red solid.

EXAMPLE 6

4,4-Difluoro-1,3-dimethyl-5-((E)-2-(3,4,5-trimethoxyphenyl)ethen-1-yl)-4-bora-3a,4a-diaza-s-indacene Compound 6

This is prepared in the same manner as described in Example 3 from 3,5-dimethylpyrrole-2-carboxaldehyde (14 mg, 0.11 mmol) and 2-((E)-2-(3,4,5,-trimethoxyphenyl)ethen-1-yl)pyrrole (Compound 26, 40 mg, 0.11 mmol). Compound 6 (9 mg, 20%) is obtained as a dark red solid.

EXAMPLE 7

4,4-Difluoro-1,3-dimethyl-5-((E)-2-(3,5-dimethyl-4-isoxazolyl)ethen-1-yl)-4-bora-3a,4a-diaza-s-indacene Compound 7

This is prepared in the same manner as described in Example 3 from 3,5-dimethylpyrrole-2-carboxaldehyde (32 mg, 0.26 mmol) and 2-((E)-2-(3,4-dimethyl-4-isoxazolyl)ethen-1-yl)pyrrole (Compound 27, 50 mg, 0.27 mmol). Compound 7 (25 mg, 28%) is obtained as a purple red solid.

EXAMPLE 8

4,4-Difluoro-5,7-dimethyl-3-((E)-2-(5-carbomethoxy-4-methyl-2-oxazolyl)ethen-1-yl)-4-bora-3a,4a-diaza-s-indacene Compound 8

This is prepared in the same method as described in Example 3 from 3,5-dimethylpyrrole-2-carboxaldehyde (159 mg, 1.29 mmol) and 2-((E)-2-(5-carbomethoxy-4-methyl-2-oxazolyl)ethen-1-yl)pyrrole (Compound 28, 300 mg, 1.29 mmol). Compound 8 (179 mg, 37%) is obtained as a dark purple solid.

EXAMPLE 9

4,4-Difluoro-1,3-dimethyl-5-((E)-2-(1-naphthyl)ethen-1-yl)-4-bora-3a,4a-diaza-s-indacene Compound 9

This is prepared in the same manner as described in Example 3 from 3,5-dimethylpyrrole-2-carboxaldehyde (28 mg, 0.23 mmol) and 2-((E)-2-(1-naphthyl)ethen-1-yl)pyrrole (Compound 29, 50 mg, 0.23 mmol). Compound 9 (32 mg, 38%) is obtained as a dark purple red solid.

EXAMPLE 10

4,4-Difluoro-5,7-dimethyl-3-((E)-2-(4-carbomethoxyphenyl)ethen-1-yl)-4-bora-3a,4a-diaza-s-indacene Compound 10

This is prepared in the same manner as described in Example 3 from 3,5-dimethylpyrrole-2-carboxaldehyde (270 mg, 2.20 mmol) and 2-((E)-2-(4-carbomethoxyphenyl)ethen-1-yl)pyrrole (Compound 30, 500 mg, 2.19 mmol). Compound 10 (240 mg, 29%) is obtained as a dark red solid.

EXAMPLE 11

4,4-Difluoro-5,7-dimethyl-3-((E)-2-carbomethoxyethen-1-yl)-4-bora-3a,4a-diaza-s-indacene (Compound 11

To a solution of 400 mg (3.25 mmol) of 3,5-dimethylpyrrole-2-carboxaldehyde and 500 mg (3.30 mmol) of 2-((E)-2-carbomethoxyethen-1-yl)pyrrole, Compound 31 in 5 mL of hexane and 10 mL of dichloromethane is added 310 μL (3.33 mmol) of phosphorus oxychloride while the reaction mixture is stirred at ice bath temperature. It is stirred at ice bath temperature for 2 hours and is added 2.30 g (10.7 mmol) of 1,8-bis(dimethylamino)naphthalene, followed by addition of 2.0 mL (16.3 mmol) of boron trifluoride etherate. After the mixture is stirred at room temperature for 12 hours, it is filtered and the resulting filtrate is concentrated to give a crude product. It is purified by chromatography on silica gel with 1:1 hexane/chloroform as eluant to give 300 mg (30%) of Compound 11 as a dark red solid.

EXAMPLE 12

4,4-Difluoro-1,3-dimethyl-5-(4-phenyl-1,3-butadien-1-yl)-4-bora-3a,4a-diaza-s-indacene Compound 12

This is prepared in the same manner as described in Example 3 from 3,5-dimethylpyrrole-2-carboxaldehyde (30 mg, 0.24 mmol) and 2-(4-phenyl-1,3-butadien-1- yl)pyrrole (Compound 32, 50 mg, 0.25 mmol). Compound 12 (29 mg, 34%) is obtained as a dark purple solid.

EXAMPLE 13

4,4-Difluoro-3,5-bis((E)-2-phenylethen-1-yl)-4-bora 3a,4a-diaza-s-indacene

Compound 13

This is prepared in the same manner as described in Example 3 from 2-((E)-2-phenylethen-1-yl)pyrrole (Compound 23, 100 mg, 0.59 mmol) and 2-formyl-5-((E)-2-phenylethen-1-yl)pyrrole (Compound 33, 110 mg, 0.59 mmol). Compound 13 (55 mg, 23%) is obtained as a dark blue solid.

EXAMPLE 14

4,4-Difluoro-3-((E)-2-phenylethen-1-yl)-5-(2-pyrrolyl)-4-bora-3a,4a-diaza-s-indacene Compound 14

This is prepared in the same manner as described in Example 3 from 2,2'-bipyrrole (100 mg, 0.76 mmol) and 2-formyl-5-((E)-2-phenylethen-1-yl)pyrrole (Compound 33, 140 mg, 0.75 mmol). Compound 14 (14 mg, 5%) is obtained as a dark blue solid.

EXAMPLE 15

4,4-Difluoro-3-((E)-2-(3,5-dimethyl-4-isoxazolyl)ethen-1-yl-5-((E)-2-phenylethen-1-yl)-4-bora-3a,4a-diaza-s-indacene Compound 15

This is prepared in the same manner as described in Example 3 from 2-formyl-5-((E)-2-phenylethen-1-yl)pyrrole (Compound 33, 50 mg, 0.26 mmol) and 2-((E)-2-(3,5-dimethyl-4isoxazolyl)ethen-1-yl)pyrrole (Compound 27, 50 mg, 0.26 mmol). Compound 15 (33 mg, 31%) is obtained as a dark blue solid.

EXAMPLE 16

4,4-Difluoro-1,3-diphenyl-5-((E)-2-(3,5-dimethyl-4-isoxazolyl)ethen-1-yl)-4-bora-3a,4a-diaza-s-indacene Compound 16

This is prepared in the same manner as described in Example 3 from 3,5-diphenylpyrrole-2-carboxaldehyde (65 mg, 0.26 mmol) and 2-((E)-2-(3,5-dimethyl-4-isoxazolyl)ethen-1-yl)pyrrole (Compound 27, 50 mg, 0.26 mmol). Compound 16 (27 mg, 22%) is obtained as a dark blue solid.

EXAMPLE 17

4,4-Difluoro-1,3-diphenyl-5-((E)-2-phenylethen-1-yl)-4-bora-3a,4a-diaza-s-indacene Compound 17

This is prepared in the same manner as described in Example 3 from 3,5-diphenylpyrrole-2-carboxaldehyde (145 mg, 0.59 mmol) and 2-((E)-2-phenylethen-1-yl)pyrrole (Compound 23, 100 mg, 0.59 mmol). Compound 17 is obtained as a dark blue solid.

EXAMPLE 18

4,4-Difluoro-3,5-bis(4-phenyl-1,3-butadien-1-yl)-4-bora-3a,4a-diaza-s-indacene

Compound 18

This is prepared in the same manner as described in Example 3 from 2-(4-phenyl-1,3-butadien-1-yl)pyrrole (Compound 32, 43 mg, 0.22 mmol) and 2-formyl-5-(4-phenyl-1,3-butadien-1-yl)pyrrole (Compound 34, 50 mg, 0.22 mmol). Compound 18 (29 mg, 29%) is obtained as a dark blue solid.

EXAMPLE 19

4,4-Difluoro-3-(4-phenyl-1,3-butadien-1-yl)-5-((E)-phenylethen-1-yl)4-bora-3a,4a-diaza-s-indacene Compound 19

This is prepared in the same manner as described in Example 3 from 2-formyl-5-((E)-phenylethen-1-yl)pyrrole (Compound 23, 48 mg, 0.26 mmol) and 2-(4-phenyl-1,3-butadien-1-yl)pyrrole (Compound 32, 50 mg, 0.26 mmol). Compound 19 (38 mg, 37%) is obtained as a dark blue solid.

EXAMPLE 20

4,4-Difluoro-3,5-bis((E)-2-(1-naphthyl)ethen-1-yl)-4-bora-3a,4a-diaza-s-indacene Compound 20

This is prepared in the same manner as described in Example 3 from 2-((E)-2-(1-naphthyl)ethen-1-yl)pyrrole (Compound 29, 50 mg, 0.23 mmol) and 2-formyl-5-((E)-2-(1-naphthyl)ethen-1-yl)pyrrole (Compound 35, 56 mg, 0.23 mmol). Compound 20 (45 mg, 40%) is obtained as a dark blue solid.

EXAMPLE 21

2-((E)-Propen-1-yl)pyrrole

Compound 21

To a stirred solution of sodium (1.5 g, 65.2 mmol) in 10 mL of methanol is added a solution of ethyl triphenylphosphonium bromide (23 g, 62.0 mmol) in 10 mL of methanol and 100 mL of dry tetrahydrofuran at room temperature over a period of 15 minutes. After addition of a solution of pyrrole-2-carboxaldehyde (5.0 g, 52.6 mmol) in 50 mL of dry tetrahydrofuran, the reaction mixture is heated at reflux under a nitrogen atmosphere for 15 hours. After cooling to room temperature, the reaction mixture is filtered through a diatomaceous earth pad and the filtrate is concentrated under vacuum to give an oil. This is purified by silica gel column chromatography with 1:1 hexane/chloroform as eluant to give 3.93 g (70%) of a pale yellow oil as a mixture of trans- and cis-isomers. $^1$H NMR analysis showed that the product contained 82% of the desired trans-isomer.

Compounds 22, 29 and 31 are prepared in a similar way as described in Example 21 by the reaction of cyanomethyl triphenylphosphonium chloride, 1-naphthylmethyl triphenylphosphonium chloride and (carbomethoxymethylene)triphenylphosphorane, respectively, with pyrrole-2-carboxaldehyde.

EXAMPLE 22

2-((E)-2-(4-Carbomethoxyphenyl)ethen-1-yl)pyrrole

Compound 30

A mixture of 1.0 g (10.5 mmol) of pyrrole-2-carboxaldehyde, 2.5 g (10.9 mmol) of methyl 4-bromomethylbenzoate, 2.2 g (10.9 mmol) of tributylphosphine and 700 mg of zinc is heated at 100° C. in a stream of nitrogen for 15 hours. After cooling to room temperature, the whole reaction mixture is treated with 50 mL of chloroform. It is washed several times (3×50 mL) with water. The organic layer is dried with anhydrous sodium sulfate and concentrated under reduced pressure. The crude product is purified by chromatography on silica gel with 30% chloroform in hexane as eluant to give 427 mg (18%) of Compound 30.

Compounds 23, 24, 25, 26, 27, 28 and 32 are prepared by the reaction of benzyl chloride, 4-methoxybenzyl chloride, 3-methoxybenzyl chloride, 3,4,5-trimethoxybenzyl chloride, 4-chloromethyl-3,5-dimethylisoxazole, 5-carbomethoxy-2-chloromethyl-4-methyloxazole and cinnamyl chloride, respectively, with pyrrole-2-carboxaldehyde as described in Example 22.

EXAMPLE 23

2-Formyl-5-((E)-phenylethen-1-yl)pyrrole

Compound 33

To an ice cooled 1 mL of dimethylformamide is added 600 μL (6.3 mmol) of phosphorus oxychloride while stirring under a nitrogen atmosphere. The mixture is stirred 15 minutes and then 5 mL of 1,2-dichloroethane is added. To this mixture is added a solution of 1.0 g (5.9 mmol) of 2-((E)-phenylethen-1-yl)pyrrole, Compound 23, in 5 mL of 1,2-dichloroethane while cooling in an ice bath. The reaction mixture is then heated under reflux for 15 minutes. After cooling to room temperature, a solution of sodium acetate trihydrate (7.0 g, 51.5 mmol) in 50 mL of water is added to the mixture. After heating under reflux for 15 minutes, the mixture is cooled and the 1,2-dichloroethane layer is separated. The aqueous layer is extracted with chloroform. The combined organic extracts are washed with saturated aqueous sodium carbonate solution and dried over anhydrous sodium carbonate. Following evaporation of solvent under vacuum, the crude product is purified by silica gel chromatography with chloroform as eluant, giving 0.87 g (75%) of Compound 33.

Compounds 34, 35 and 36 are prepared from Compounds 32, 29 and 31, respectively, as described in Example 23.

EXAMPLE 24

2-(1-Phenylethen-1-yl)pyrrole

Compound 37

A mixture of benzoic acid (2.3 g, 18.8 mmol), 2,2'-dipyridyldisulfide (6.1 g, 27.7 mmol) and triphenylphosphine (7.3 g, 27.5 mmol) in 30 mL of dry toluene is stirred at room temperature under argon for 1 day. The reaction mixture is cooled to −78° C. and dropwise treated with pyrrylmagnesium chloride (prepared from 20 mL, 3.0M methylmagnesium chloride in tetrahydrofuran and 4.1 g (61.1 mmol) of pyrrole in 180 mL of toluene at −40° C. by the method of K. C. Nicolaou, et al. Tetrahedron Letters 22, 4647 (1981)). After stirring at −78° C. for 1 hour, the reaction mixture is quenched with 200 mL of saturated aqueous ammonium chloride solution and extracted with three portions of 200 mL of ether. The combined ether extracts are washed with 5% aqueous potassium carbonate (3×200 mL), water (3×200 mL) and finally with brine (3×200 mL). The organic layer is separated, dried over anhydrous sodium sulfate and concentrated under vacuum to give a crude product. This is purified by silica gel chromatography to give 2-benzoylpyrrole, as an intermediate. This is converted to Compound 37 by the standard Wittig reaction (as described in Example 21) using methyl triphenylphosphonium bromide and sodium methoxide in tetrahydrofuran solution.

EXAMPLE 25

2-(1-(2-Thienyl)ethen-1-yl)pyrrole

Compound 38

This is prepared in the same manner as described in Example 24 using thiophene-2-carboxylic acid instead of benzoic acid.

EXAMPLE 26

4,4-Difluoro-5,7-diphenyl-3-((E)-2-carbomethoxyethen-1-yl)-4-bora-3a,4a-diaza-s-indacene Compound 39

This is prepared in the same manner as described in Example 3 from 2,4-diphenylpyrrole (50 mg, 0.23 mmol) and 2-((E)-2-carbomethoxyethen-1-yl)-5-formylpyrrole (Compound 36, 45 mg, 0.25 mmol). Compound 37 (24 mg, 25%) is obtained as a dark purple solid.

EXAMPLE 27

4,4-Difluoro-3,5-bis((E)-2-phenylethen-1-yl)-4-bora-3a,4a-diaza-s-indacene

Compound 40

To a solution of 2-((E)-2-phenylethen-1-yl)pyrrole (Compound 23, 1.0 g, 5.90 mmol) in 30 mL of dichloromethane is added freshly distilled acetyl chloride (210 μL, 2.95 mmol) dropwise and the reaction mixture is heated under reflux for 15 hours. It is cooled to room temperature and is added N,N-diisopropylethylamine (2.0 mL, 12.1 mmol), followed by addition of boron trifluoride etherate (1.4 mL, 11.4 mmol). The whole mixture is stirred at room temperature for 2 hours and is worked up and purified as described in Example 1 to obtain Compound 40.

EXAMPLE 28

4,4-Difluoro-8-((E)-2-phenylethen-1-yl)-1,3,5,7-tetramethyl-4-bora-3a,4a-diaza-s-indacene Compound 41

To a solution of 2,4-dimethylpyrrole (1.4 g, 15.0 mmol) and trans-cinnamaldehyde (1.0 g, 7.5 mmol) in 30 mL of dichloromethane is added phosphorus oxychloride (0.75 mL, 8.0 mmol) and the whole reaction mixture is heated under reflux for 20 hours. It is cooled to room temperature and is added N,N-diisopropylethylamine (5.7 mL, 32.7 mmol), followed by addition of boron trifluoride etherate (4.0 mL, 32.5 mmol). After stirring at room temperature for 3 hours, it is worked up and purified as described in Example 1 to obtain Compound 41.

EXAMPLE 29

4,4-Difluoro-1,3-dimethyl-5-(1-phenylethen-1-yl)-4-bora-3a,4a-diaza-s-indacene

Compound 42

This is prepared in the same manner as described in Example 3 from 3,5-dimethylpyrrole-2-carboxaldehyde and 2-(1-phenylethen-1-yl)pyrrole, Compound 37.

EXAMPLE 30

4,4-Difluoro-1,3-dimethyl-5-(1-(2-thienyl)ethen-1-yl)-4-bora-3a,4a-diaza-s-indacene Compound 43

This is prepared in the same manner as described in Example 3 from 3,5-dimethylpyrrole-2-carboxaldehyde and 2-(1-(2-thienyl)ethen-1-yl)pyrrole, Compound 38.

EXAMPLE 31

Spectral Characterization of New Ethenyl-Substituted Dipyrromethenboron Difluoride Dyes $^1$H NMR spectra are measured using a Nicolet QE-300 MHz (General Electric) spectrometer for solutions in CDCl$_3$ (unless otherwise stated), with tetramethylsilane (TMS) as an internal standard. Chemical shifts are given in ppm from TMS and splitting patterns are designated as: s, singlet; d, doublet; t, triplet; m, multiplet. Results of spectral data for representative new ethenyl-substituted dipyrromethenboron difluoride dyes and ethenyl-substituted pyrrole intermediates are given in Table 4 and Table 5, respectively.

Absorption spectra are obtained by dissolving the dye at a concentration of approximately $5 \times 10^{-6}$M in an appropriate solvent including but not limited to methanol, chloroform, acetonitrile, acetone or hexane, then using an IBM 9429 UV/visible spectrophotometer. Extinction coefficients ($\epsilon$) of the dyes at their absorption maxima are determined by standard Beer's law calculations. Results of the spectral determination for representative ethenyl-substituted dipyrromethenboron difluoride dyes are tabulated in Table 3 and Table 6.

Fluorescence of new ethenyl-substituted dipyrromethenboron difluoride dyes is determined by dissolving the dye at a concentration of above $1 \times 10^{-10}$M (optimum concentration ranges, $10^{-6} \sim 10^{-7}$M) in an appropriate solvent including but not limited to methanol, water, ethanol, acetonitrile, acetone, chloroform, toluene or hexane then using a Perkin-Elmer Model 650-40 fluorescence spectrophotometer equipped with a Perkin-Elmer/Hitachi 057 X-Y recorder. Results of the spectral determination for representative ethenyl-substituted dipyrromethenboron difluoride dyes are summarized in Table 3 and Table 6. Fluorescence can also be observed for the dyes in solution or on thin layer chromatography (TLC) plates, by visual inspection with illumination by a suitable source that gives off light below 650 nm.

EXAMPLE 32

Photobleaching Studies

Photostability measurements of ethenyl-substituted dipyrromethenboron difluoride dyes are conducted in acetonitrile solution with continuous illumination by a 250 watt xenon arc lamp with 20 nm slit width at the corresponding wavelength (485 nm for Compound R and Compound 11, 545 nm for Compound 3 and Compound 12, 600 nm for Compound 13 and Compound 18). After fifteen minutes of continuous illumination while stirring at room temperature in a cuvette of fluorometer, emission intensity data is collected with 2.5 nm slit width at the emission maxima of individual samples. The results are listed in Table 6, together with that of the alkyl-substituted dipyrromethenboron difluoride dye, Compound R, for comparison (also shown in FIG. 4). Concentrations of individual samples are prepared to have the same optical density for all of the dyes at the respective absorption wavelength.

It will be obvious to one skilled in the art that synthesis of many other 4,4-difluoro-4-bora-3a,4a-diaza-s-indacene dyes that contain other ethenyl substituents can be accomplished using other ethenyl pyrrole precursors that contain substituents compatible with the chemistry in FIG. 1 and such ethenyl-substituted 4,4-difluoro-4-bora-3a,4a-diaza-s-indacene dyes from other ethenyl pyrrole precursors will fall within the description of the invention.

What is claimed is:

1. A compound of the general formula:

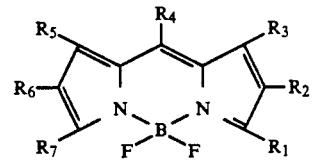

wherein at least one of the fluorophore substituents R$_1$–R$_7$ is an initial ethenyl group having initial ethenyl substituents; or a conjugated dienyl group having initial and secondary ethenyl substituents; or a conjugated trienyl group having initial, secondary and tertiary ethenyl substituents, and where said initial, secondary, and tertiary ethenyl substituents which may be the same or different, are hydrogen; halogen; alkyl (containing 1–10 carbon atoms); cyano; carboxylate ester; carboxamide; or aryl or heteroaryl, where said heteroaryl is pyrrole, thiophene, furan, oxazole, isoxazole, oxadiazole, imidazole, benzoxazole, benzothiazole, benzimidazole, benzofuran, or indole, which aryl or heteroaryl may be further substituted, one or more times, by alkyl (containing 1–5 carbon atoms), or alkoxy groups the alkyl portions of which groups have less than 5 carbon atoms, or combinations thereof; and the remaining fluorophore substituents R$_1$–R$_7$ that are non-ethenyl, -dienyl, or -trienyl, which may be the same or different, are hydrogen; alkyl (containing 1–18 carbon atoms); acyl; sulfo; arylalkyl, the alkyl portion of which contains 1–18 carbon atoms; or aryl or heteroaryl, which may be further substituted, one or more times, by alkyl (containing 1–5 carbon atoms), or alkoxy or dialkylamino groups wherein the alkyl portions of such groups have less than 5 carbon atoms, or combinations thereof;

said compound having an absorption maximum at a wavelength longer than about 525 nm.

2. A compound, as claimed in claim 1, where there is one initial ethenyl group of the formula —CX=CY—Z, located at R$_1$, R$_2$, R$_3$, or R$_4$;

at least one of the corresponding initial ethenyl substituents X, Y, or Z, which may be the same or different, is hydrogen;

at least one other of the corresponding initial ethenyl substituents is hydrogen; halogen; alkyl (containing 1–10 carbon atoms); cyano; carboxylate ester; carboxamide; or aryl or heteroaryl, which may be further substituted, one or more times; and the remaining six non-ethenyl fluorophore substituents at R$_{1-7}$, which may be the same or different, are hydrogen; alkyl (containing 1–5 carbon atoms);

aryl; heteroaryl; or aryl or heteroaryl that is further substituted, one or more times.

3. A compound, as claimed in claim 2, where the initial ethenyl group is located at $R_1$, $R_2$, or $R_3$; and
at least one of the corresponding initial ethenyl substituents is aryl or heteroaryl; or aryl or heteroaryl that is further substituted, one or more times.

4. A compound, as claimed in claim 3, where the initial ethenyl substituent Z is heteroaryl which heteroaryl may be further substituted, one or more times.

5. A compound, as claimed in claim 3, where the initial ethenyl substituent Z is aryl that is phenyl; 1-napthyl; 2-naphthyl; 1-pyrenyl; or 9-anthryl; which aryl may be further substituted, one or more times.

6. A compound, as claimed in claim 2, where the initial ethenyl group is located at $R_4$ and X, Y, or Z is aryl or heteroaryl; or aryl or heteroaryl that is further substituted one or more times.

7. A compound, as claimed in claim 6, where the initial ethenyl substituent Z is aryl that is phenyl; 1-naphthyl; 2-naphthyl; 1-pyrenyl; or 9-anthryl; which aryl may be further substituted, one or more times.

8. A compound, as claimed in claim 6, where the initial ethenyl substituent Z is heteroaryl; which heteroaryl may be further substituted, one or more times.

9. A compound, as claimed in claim 1, where there are two initial ethenyl groups symmetrically located at $R_1$ and $R_7$, $R_2$ and $R_6$, or $R_3$ and $R_5$, each having the formula $-CX=CY-Z$;
at least one of the three corresponding initial ethenyl substituents X, Y and Z from each symmetrical ethenyl group, which may be the same or different, is hydrogen; and
at least one other of the three corresponding initial ethenyl substituents from each symmetrical ethenyl group, which may be the same or different, is hydrogen; halogen; alkyl (containing 1-10 carbon atoms); cyano; carboxylate ester; carboxamide; or aryl or heteroaryl, which may be further substituted, one or more times; and
the remaining five non-ethenyl fluorophore substituents at $R_{1-7}$, which may be the same or different, are hydrogen; alkyl (containing 1-5 carbon atoms); aryl; heteroaryl; or aryl or heteroaryl that is further substituted, one or more times.

10. A compound, as claimed in claim 9, where at least one of the six corresponding initial ethenyl substituents, which may be the same or different, is aryl or heteroaryl; or aryl or heteroaryl that is further substituted, one or more times.

11. A compound, as claimed in claim 10, where at least two of the six corresponding initial ethenyl substituents, which may be the same or different, are aryl or heteroaryl; or aryl or heteroaryl that is further substituted, one or more times.

12. A compound, as claimed in claim 11, where the corresponding initial ethenyl substituents Z, from each of the symmetrically located initial ethenyl groups, are each heteroaryl, which may be the same or different, which heteroaryl may be further substituted, one or more times.

13. A compound, as claimed in claim 11, where the initial ethenyl substituents Z, from each of the symmetrically located initial ethenyl groups, are each aryl, which may be the same or different, where each aryl is phenyl; 1-naphthyl; 2-naphthyl; 1-pyrenyl; or 9-anthryl; which aryl may be further substituted, one or more times.

14. A compound, as claimed in claim 11, where each initial ethenyl substituent that is aryl, which may be the same or different, is phenyl; 1-naphthyl; 2-naphthyl; 1-pyrenyl; or 9-anthryl; which aryl may be further substituted, one or more times.

15. A compound, as claimed in claim 1, where there is one conjugated dienyl group having initial and secondary ethenyl substituents; or conjugated trienyl group having initial, secondary and tertiary ethenyl substituents located at $R_1$, $R_2$, $R_3$, or $R_4$;
at least one of the corresponding initial ethenyl substituents is hydrogen; and
at least one of the corresponding secondary ethenyl substituents is hydrogen.

16. A compound, as claimed in claim 15, where the conjugated dienyl or trienyl group has the formula: $-CX=CY-(CH=CH)_n-Z$, where $n=0$ or 1;
the secondary or tertiary ethenyl substituent Z is aryl; heteroaryl; or aryl or heteroaryl that is further substituted, one or more times; and
the remaining six non-dienyl or -trienyl fluorophore substituents at $R_{1-7}$ are hydrogen; alkyl (containing 1-5 carbon atoms); aryl; heteroaryl; or aryl or heteroaryl that is further substituted, one or more times.

17. A compound, as claimed in claim 1, where there are two conjugated dienyl or trienyl groups symmetrically substituted at $R_1$ and $R_7$, $R_2$ and $R_6$, or $R_3$ and $R_5$;
at least one of the three corresponding initial ethenyl substituents from each symmetrical dienyl or trienyl group, which may be the same or different, is hydrogen; and
at least one of the corresponding secondary ethenyl substituents from each symmetrical group, which may be the same or different, is hydrogen.

18. A compound, as claimed in claim 17, where each of the symmetrically located conjugated dienyl or trienyl groups, which may be the same or different, has the formula: $-CX=CY-(CH=CH)_n-Z$, where $n=0$ or 1;
the corresponding secondary or tertiary ethenyl substituents Z, which may be the same or different, are aryl; heteroaryl; or aryl or heteroaryl that is further substituted, one or more times; and
the remaining five non-ethenyl fluorophore substituents at $R_{1-7}$ are hydrogen; alkyl (containing 1-5 carbon atoms); or aryl or heteroaryl, which may be further substituted, one or more times.

19. A compound, as claimed in claim 18, where each substituent that is aryl, which may be the same or different, is phenyl; 1-naphthyl; 2-naphthyl; 1-pyrenyl; or 9-anthryl; which aryl may be further substituted, one or more times.

20. A compound of the general formula:

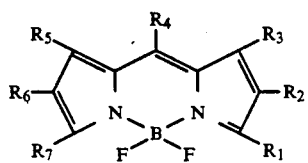

wherein one or two of the fluorophore substituents $R_1$-$R_7$ is an initial ethenyl or conjugated dienyl or trienyl group of the formula $-(CH=CH)_n-Z$, where n is 1, 2, or 3, where one or two of the corresponding initial, secondary, or tertiary ethenyl substituents Z, which may be the same or different, are hydrogen; halogen; alkyl (containing 1-10 carbon atoms); cyano; carboxylate ester; carboxamide; or aryl that is phenyl, 1-naphthyl, 2-naphthyl, 1-pyrenyl, or 9-anthryl; or heteroaryl that is pyrrole, thiophene, furan, oxazole, isoxazole, oxadiazole, imidazole, benzoxazole, benzothiazole, benzimidazole, benzofuran, or indole; which aryl or heteroaryl may be further substituted, one or more times, by alkyl (containing 1-5 carbon atoms), or alkoxy groups the alkyl portions of which groups have less than 5 carbon atoms, or combinations thereof and the remaining five or six fluorophore substituents $R_1$-$R_7$ that are non-ethenyl, dienyl, or trienyl, which may be the same or different, are hydrogen; halogen; alkyl (containing 1-18 carbon atoms); acyl; sulfo; arylalkyl, the alkyl portion of which contains 1-18 carbon atoms; or aryl that is phenyl, 1-naphthyl, 2-naphthyl, 1-pyrenyl, or 9-anthryl; or heteroaryl that is pyrrole, thiophene, furan, oxazole, isoxazole, oxadiazole, imidazole, benzoxazole, benzothiazole, benzimidazole, benzofuran, or indole; which aryl or heteroaryl may be further substituted, one or more times, by alkyl (containing 1-5 carbon atoms), or alkoxy or dialkylamino groups wherein the alkyl portions of such groups have less than 5 carbon atoms, or combinations thereof;

said compound having an absorption maximum at a wavelength longer than about 530 nm and an emission maximum at a wavelength longer than about 550.

* * * * *

UNITED STATES PATENT AND TRADEMARK OFFICE
CERTIFICATE OF CORRECTION

PATENT NO. : 5,187,288
DATED : February 16, 1993
INVENTOR(S) : Kang, et al.

It is certified that error appears in the above-indentified patent and that said Letters Patent is hereby corrected as shown below:

At col 3, line 47-54, "[FORMULA I]" should appear at the left margin, below the structural formula.

At col 4, line 36, "$X"_{mp}$," should be --$X"_{mpt}$--.

At col 4, line 37, "—$CX"_{mpt}$—$Z"_{mpt}$)," should be ---—$CX"_{mpt}$=$CY"_{mpt}$—$Z"_{mpt}$),--.

Signed and Sealed this

Seventeenth Day of September, 1996

Attest:

BRUCE LEHMAN

*Attesting Officer*    *Commissioner of Patents and Trademarks*